US006025388A

United States Patent [19]
Nagpal et al.

[11] Patent Number: 6,025,388
[45] Date of Patent: Feb. 15, 2000

[54] METHOD FOR INHIBITING GENE EXPRESSION PROMOTED BY AP1 PROTEIN WITH RARβ SELECTIVE RETINOIDS AND METHOD FOR TREATMENT OF DISEASES AND CONDITIONS WITH SUCH RETINOIDS

[75] Inventors: Sunil Nagpal, Irvine; Tae K. Song, Long Beach; Vidyasagar Vuligonda; Jyoti Athanikar, both of Irvine; Roshantha A. Chandraratna, Mission Viejo, all of Calif.

[73] Assignee: Allergan Sales, Inc., Irvine, Calif.

[21] Appl. No.: 08/428,957

[22] Filed: Apr. 26, 1995

[51] Int. Cl.[7] ............................. A01N 43/16; A01N 43/40
[52] U.S. Cl. .......................................... 514/460; 514/336
[58] Field of Search ..................... 514/460, 336

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Schroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/435 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |

(List continued on next page.)

FOREIGN PATENT DOCUMENTS

| | | | |
|---|---|---|---|
| 0098591 | 1/1984 | European Pat. Off. | C07D 333/54 |
| 0130795 | 1/1985 | European Pat. Off. | C07D 311/58 |
| 170105A | 2/1986 | European Pat. Off. | |
| 0176032 | 4/1986 | European Pat. Off. | C07C 65/38 |
| 0176033 | 4/1986 | European Pat. Off. | C07D 261/18 |
| 176034A | 4/1986 | European Pat. Off. | C07C 63/66 |
| 0253302 | 1/1988 | European Pat. Off. | C07D 213/16 |
| 0272921 | 6/1988 | European Pat. Off. | C07D 213/80 |
| 0284288 | 9/1988 | European Pat. Off. | C07D 401/04 |
| 0303915 | 2/1989 | European Pat. Off. | A61K 31/255 |
| 0315071 | 5/1989 | European Pat. Off. | C07C 63/66 |
| 0350846 | 7/1989 | European Pat. Off. | C07D 311/58 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 8500806 | 2/1985 | WIPO | A61K 31/00 |
| 8504652 | 10/1985 | WIPO | A61K 31/19 |
| WO9116051 | 10/1991 | WIPO | A61K 31/44 |
| WO9206948 | 4/1992 | WIPO | C07C 69/86 |

OTHER PUBLICATIONS

Yang–Yen et al. (1991) *The New Biologist*, 3/12: 1206–1219.

Karin et al. (1993) *Eur. J. Clin. Pharmacol.*, 45[Supp]: S9–S15.

Herrlich et al. (1994) *TEM*, 5/8: 341–346.

Nicholson et al. (1990) *The EMBO Journal*, 9/13: 4443–4454.

A General Synthesis of Terminal and Internal Arylalkynes by the Palladium–Catalyzed Reation of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King, and William L. Klima, *J. Org. Chem.* 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'–Diacyl–1,1'–biaryls. Regiocontrolled Protection of . . . by Mervic, et al, *J. Org. Chem.*, No. 45, pp. 4720–4725, 1980.

(List continued on next page.)

*Primary Examiner*—Russell Travers
*Attorney, Agent, or Firm*—Gabor L. Szekeres; Robert J. Baran; Martin A. Voet

[57] ABSTRACT

Retinoid compounds which repress expression of the gene promoted by AP1 protein but which do not significantly activate expression of the genes having RA-responsive elements in their promoter region through RARα and RARΓ receptor subtypes, are used, with reduced side effects, for treating diseases and conditions which are responsive to therapy with retinoids.

18 Claims, 4 Drawing Sheets

U.S. PATENT DOCUMENTS

| | | | |
|---|---|---|---|
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,426,111 | 6/1995 | Dellaria et al. | 514/272 |
| 5,426,118 | 6/1995 | Chandraratna | 514/337 |
| 5,434,173 | 7/1995 | Chandraratna | 514/354 |
| 5,534,641 | 7/1996 | Song et al. | 549/416 |

OTHER PUBLICATIONS

A Dopamine Receptor Model and Its Application in the Design of a New Class of Rigid Pyrrolo[2,3–g]isoquinoline Antipsychotics, Gary L. Olson, et al. *American Chemical Society*, 1981, Vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., *Journal of Cell Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar., 1991.

Synthesis and Evaluation of Stilbene and Dihydrostilbene Derivatives as Potential Anticancer Agents That Inhibit Tubulin Polymerization by Cushman, Mark et.al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No. 4, pp. 211–214, 1991.

Di–and Tri–methoxystyryl Derivatives of Heterocyclic Nitrogen Compounds by Bahner, C.T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

Roshantha A.S. Chandraratna, et al., "Development of RAR Subtype Selective Retinoids for Dermatological Diseases", *Eur. J. Med. Chem.*, (1995) vol. 30.

Proceedings of the 13th International Symposium on Medical Chemistry, 1994):505S–17S.

Jia–Yang Chen, et al., "RAR–specific agonist/antagonists which dissociate transactivation and API transrepression inhibit anchorage–independent cell proliferation", *The EMBO Journal*, (1995) 14/6:1187–1197.

Reuben Lotan, et al., "Retinoic Acids Receptors and Retinoid–Regulated Differentiation Markers as Intermediate Endpoints in Chemoprevention", Proceedings of the American Association for Cancer Research, (1994) vol. 35:684–685.

Andrea Fanjul, et al., "A New Class of Retinoids with Selective Inhibition of AP–1 Inhibits Proliferation", *Nature*, (1994) 372/3:107–111.

Sunil Nagpal, et al. "Spearation of Transactivation and AP1 Antagonism Functions of Retinoic Acid Receptor $\alpha^*$", *The Journal of Biological Chemistry*, (1995) 270/2:923–927.

Fanjul A. et al. "The Ying–yan of RAR and AP–1: cancer treatment without overt toxicity", *Human & Experimental Toxicology*, (1995) 14/2:226–230.

METHOD FOR INHIBITING GENE EXPRESSION PROMOTED BY AP1 PROTEIN WITH RARβ SELECTIVE RETINOIDS AND METHOD FOR TREATMENT OF DISEASES AND CONDITIONS WITH SUCH RETINOIDS

BACKGROUND OF THE INVENTION

1. Field of the Invention

The present invention is directed to a method of inhibiting gene expression promoted by the AP1 protein complex, with compounds which specifically or selectively transactivate RARβ retinoid receptors. The present invention is also directed to a method of administering pharmaceutical compositions for the treatment or prevention of certain diseases and conditions which comprise a compound or ligand capable of inhibiting gene expression promoted by the AP1 protein complex through RARs, and which compound specifically or selectively induces gene expression only through the RARβ retinoid receptors. The present invention is further directed to a method of selecting compounds of beneficial retinoid-like activity by assaying candidate compounds for ability to antagonize the gene expression medicated through the AP1 protein complex to surpress the expression of gene promoted by the AP1 protein complex, and for the ability, or lack thereof of the compounds to transactivate gene expression through RARα, RARβ and RARΓ receptors.

2. Related Art

Compounds having retinoic acid like (retinoid-like) biological activity have been known for a long time, and are described in numerous United States and foreign patents and scientific publications. Generally speaking, it has been established and accepted in the art that retinoic-acid like compounds (retinoids) are useful in humans and domestic animals for the treatment or prevention of many diseases and conditions, as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

A classic measure of retinoic-acid like activity involves the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, it was recognized early in the art that if ODC activity could be inhibited, cell hyperproliferation could be modulated. Although all causes for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Res: 1662–1670,1975 has been extensively used in the art to demonstrate inhibition of TPA induction of ODC by tests compounds, which compound, if found inhibitory in the assay, is considered a "retinoid". Several other assays also exist in the art to determine if a compound has retinoid-like biological activity.

The use of retinoids in therapy of humans or domestic animals, is however, usually not without unpleasant or even serious side effects. Therefore, efforts have been made in the art to develop compounds which retain the beneficial activity of retinoids, but nevertheless lack the undesired side effects. U.S. Pat. No. 5,324,840 (assigned to the same assignee as the present application) for example discloses compounds which have retinoid-like activity but either lack, or have diminished skin-toxicity or teratogenic activity. An application for United States patent titled "Method of Treatment with Compounds Having Selective Agonist-like Activity on RXR Retinoid Receptors" Ser. No. 08/016,404 has been allowed and is expected to issue.

Significant efforts have also been made in the prior art to elucidate, on a biological, pharmacological or molecular level, the mechanisms by which retinoids act in living organisms, and specifically by which retinoids act to bring about beneficial therapeutic results and the undesired side effects. In connection with the foregoing it has been established in the prior art that one mode of action of retinoids is inducing gene expression through a class of receptors which are termed "RAR", another is through a class of receptors termed "RXR". Both the RAR and RXR receptor "families" have been shown to include several subtypes, which in the case of the RAR receptors are termed RARα, RARβ and RARΓ. Generally speaking, the following publications pertain to retinoid receptors and/or to compounds for selectively activating one or more of the receptor subtypes: D. J. Mangelsdorf et al. "Nuclear receptor that identifies a novel retinoic acid response pathway", Nature Vol 345 May 17, 1990 pp 224–229; and J. N. Rottman et al. A retinoic acid-responsive element in the apiloprotein AI gene distinguishes between two different retinoic acid response pathways, Molecular and Cellular Biology, July 1991, pp 3814–3820, M. Petkovich et al. "A human retinoic acid receptor which belongs to the family of nuclear receptor", Nature, Vol. 330, Dec. 3, 1987, pp 444–450; V. Giguere et al. "Identification of a receptor for the morphogen retinoic acid", Nature, Vol 330, Dec. 17, 1987, pp 624–629; N. Brand et al. "Identification of a second human retinoic acid receptor", Nature, Vol 332, Apr. 28, 1988, pp 850–853; A. Krast et al., "A third human retinoic acid receptor, hRAR", Proc. Natl. Acad. Sci. U.S.A., Vol 86, July 1989, pp 5310–5314; D. J. Mangelsdorf et al., "Characterization of three RXR genes that mediate the action of 9-cis-retinoic acid", Genes & Development, Vol. 6, 1992, pp. 329–344, D. J. Mangelsdorf et al. "Nuclear receptor that identifies a novel retinoic acid response pathway" Nature Vol. 345, May 17 1990, pp224–229, and International Publication WO 93 21146 (Ligand Pharmaceuticals) titled "Compounds Having Selectivity for Retinoid X Receptors".

As a still further development in the art pertaining to the mechanism of action of retinoids at the pharmacological and molecular level, it has been discovered that in the presence of a proper ligand (retinoid compound), the RARs regulate gene expression either by directly binding to the RA-responsive element (RARE) or by antagonizing the action of c-Jun/c-Fos (AP1) protein complex. More specifically, in the action of a retinoid (ligand) that acts through the RARs, one or more of the three different RAR subtypes (RARα, RARβ and RARΓ) bind to the retinoid ligand. The resulting RAR-ligand complex regulates gene expression either by activating the expression of genes containing RAREs in their promoter regions, or by inhibiting the expression of certain genes by antagonizing AP1 protein complex (c-Jun/c-Fos, hereinafter "AP1 protein" or "AP1 protein complex") mediated gene expression. (See the articles: Mangelsdorf et al. (1994). The Retinoids; Biology, Chemistry, and Medicine, pp. 219–349. Raven Press Ltd., New York; Chambon, P. (1994) Semin, Cell Biol. 5, 115–125, and Pfahl. M. (1993) Endocr. Rev. 14, 651–658). Antagonizing the AP1 protein and thereby suppressing or inhibiting expression of the AP1-promoted gene is considered a second mechanism of action of retinoids. The latter is generally considered to be beneficial from a therapeutic standpoint, because the genes stimulated by the AP1 protein are involved in hyperproliferative and inflammatory diseases such as psoriasis, rheumatoid arthritis and tumor metastases. Published International Patent Application Nos. WO 92/05447 and WO92/07072 relate to the subject of inhibiting the gene expression which is stimulated by the AP1 protein complex.

In contrast to the action of retinoid compounds (ligands) to prevent or inhibit expression of the gene promoted by AP1, the transactivation of genes containing the RAREs, on the other hand, can lead to some of the undesired side-effect of retinoids. Therefore, a need exists in the prior art to separate the two types of retinoid actions, whereby retinoid drugs of lesser toxicity and therefore of greater therapeutic benefit may be obtained.

SUMMARY OF THE INVENTION

The present invention comprises a method for binding AP1 protein in a complex with a retinoid receptor RAR which has been activated by a retinoid compound or ligand, thereby inhibiting expression of the gene promoted by the AP1 protein, in preference over activating expression of genes which include the RAREs in their promoter regions. In other words, the present invention comprises a method for selectively inhibiting expression of the gene which is promoted by the AP1 protein, without practically inducing expression of genes that are normally triggered by retinoid like compounds through the RAREs.

In another aspect, the present invention comprises the above-mentioned gene regulation method employed for therapeutic purposes with reduced side effects, such as regulation of cell proliferation and differentiation, and particularly for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating arthritis, asthma, allergies, chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

In still another aspect, the present invention comprises pharmaceutical compositions with which the above-noted methods are practiced, and which contain retinoid-like compounds capable of inhibiting AP1-promoted gene expression without causing expression of practical significance of genes having RAREs in their promoter region.

In yet another aspect, the present invention comprises a method for selecting retinoid-compounds as candidates for drugs having reduced side effects, by assaying a candidate test compound for its ability to repress AP1-protein promoted gene expression through the three RAR subtypes (RARα, RARβ and RARΓ) and for assaying the candidate test compound for its ability to transactivate gene expression through one or more of the three RARs. Compounds which inhibit AP1-protein expression through all three RAR subtypes, but transactivate only through the RARβ receptor are selected, because the RARβ receptor is practically not present in mammalian skin, and therefore side effects in the skin by the use of such compound are practically avoided.

In a further aspect, the present invention relates to the method of using the compounds which have the foregoing properties for cancer chemotherapy.

DETAILED DESCRIPTION OF THE INVENTION

Figure 1:
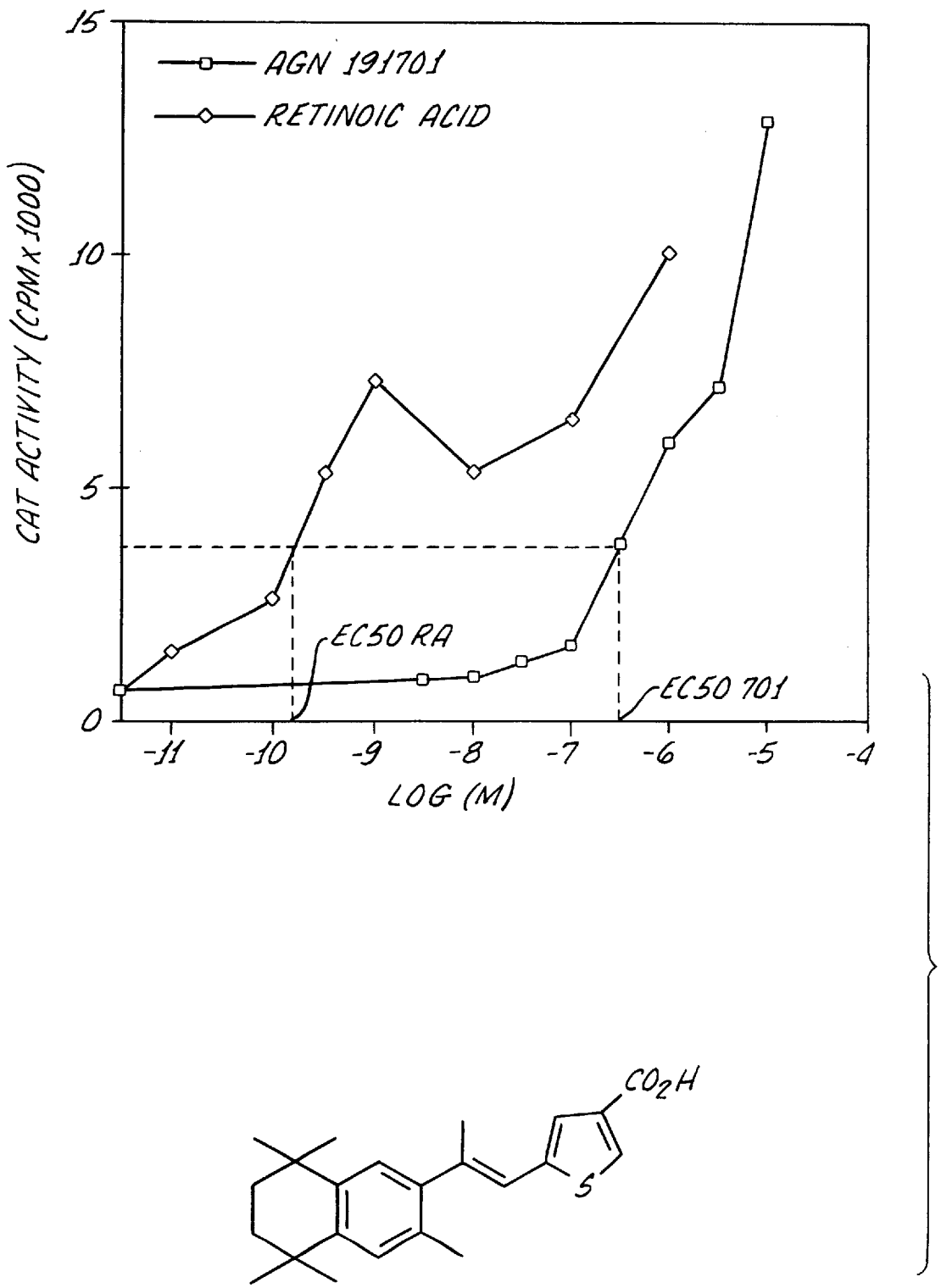
FIG. 1 is a graph showing data and the calculation of $EC_{50}$, obtained in the Cationic Liposome Mediated Transfection Assay on the $RAR_\alpha$ receptor, with an example test compound and with the reference compound trans retinoic acid.
Figure 2:
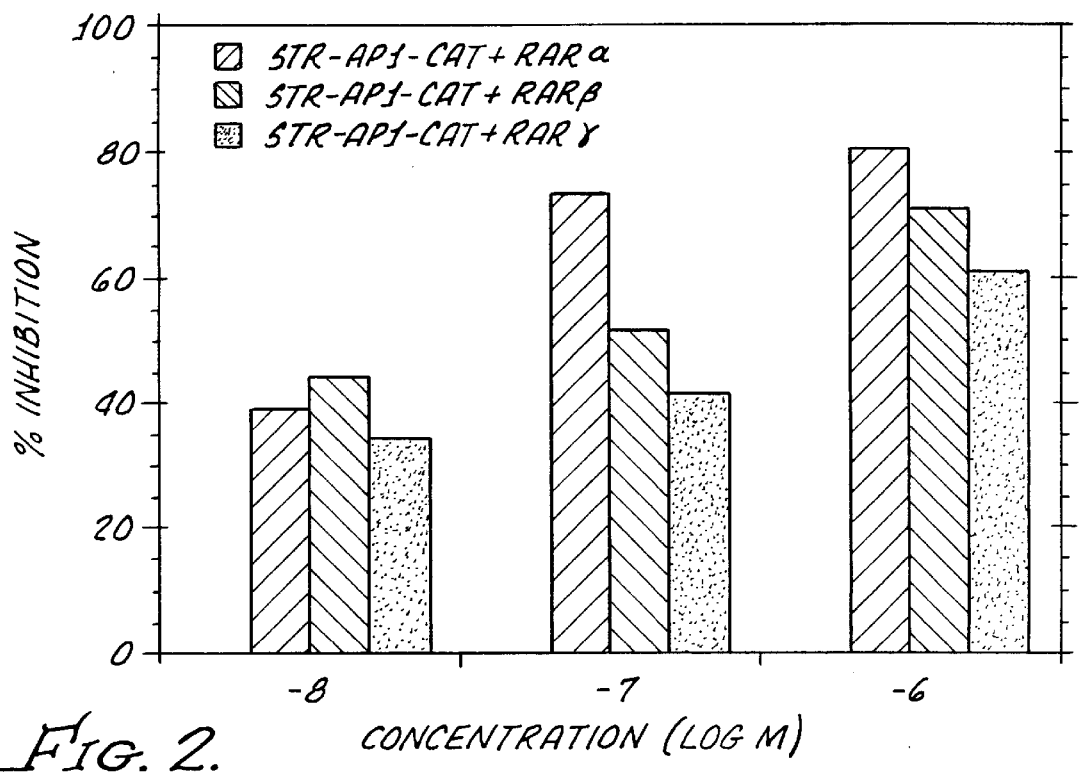
FIG. 2 is a graph showing the effect of varying concentrations of 4-[2-[[2-t-butyl-1-(2-tetrahydropyranoxy)]-4-phenyl]ethyn-1-yl]benzoic acid (Compound 2 AGN 192156) in the retinoid-mediated AP1 antagonism assay.
Figure 3:
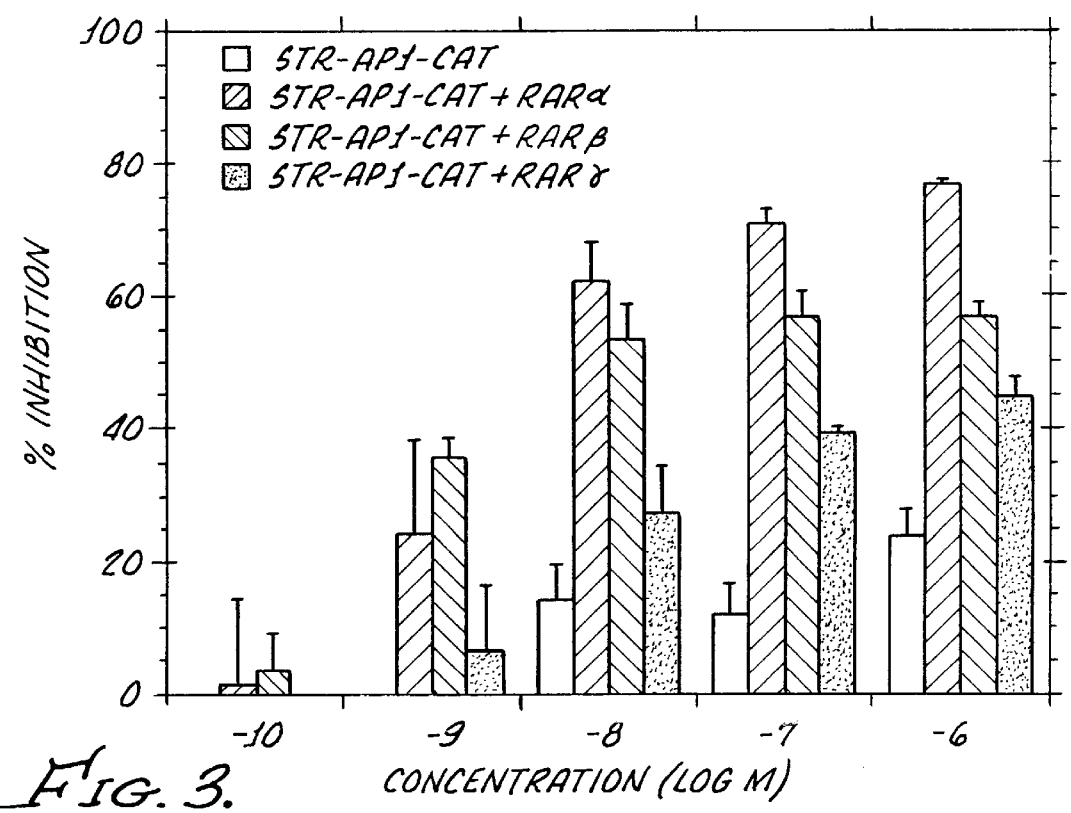
FIG. 3 is a graph showing the effect of varying concentrations of 4-[2-[[2-t-butyl-1-(2-tetrahydropyranoxy)]-5-phenyl]-ethyn-1-yl]-1-benzoic acid (Compound 7 AGN 192326) in the retinoid-mediated AP1 antagonism assay.
Figure 4:
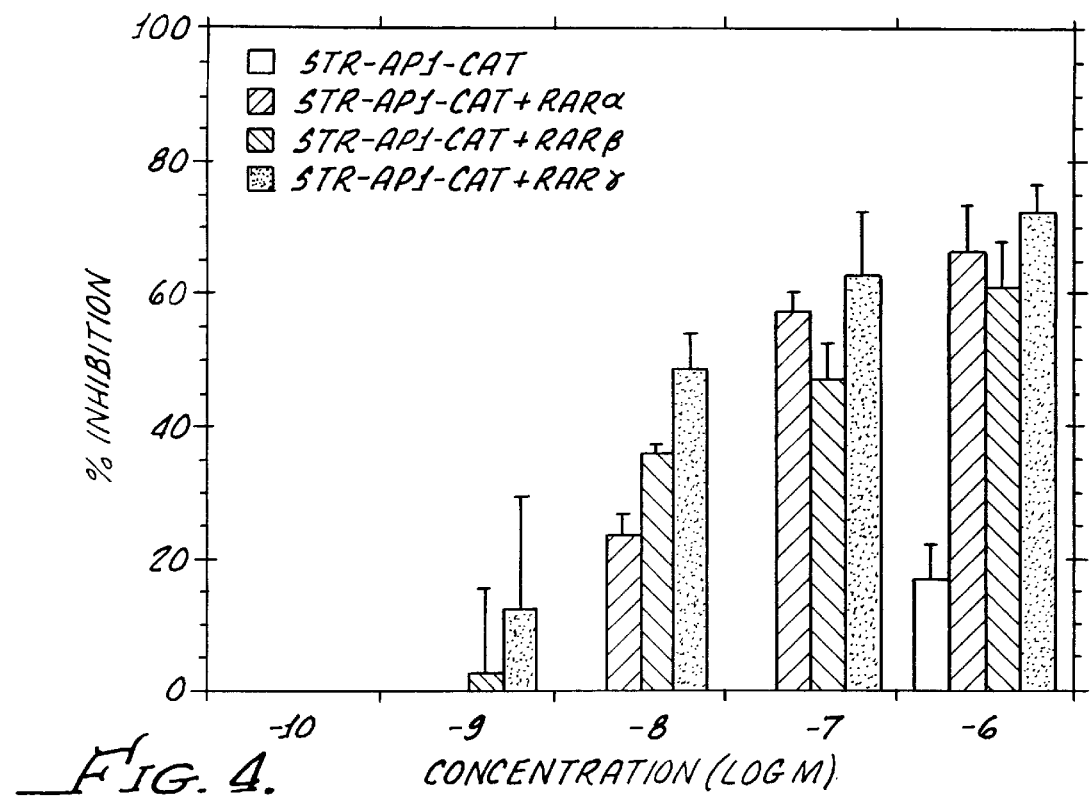
FIG. 4 is a graph showing the effect of varying concentrations of 6-[2-[[2-t-butyl-1-(2-tetrahydropyranoxy)]-5-phenyl]ethyn-1-yl]nicotinic acid (Compound 8 AGN 192327) in the retinoid-mediated AP1 antagonism assay.
Figure 5:
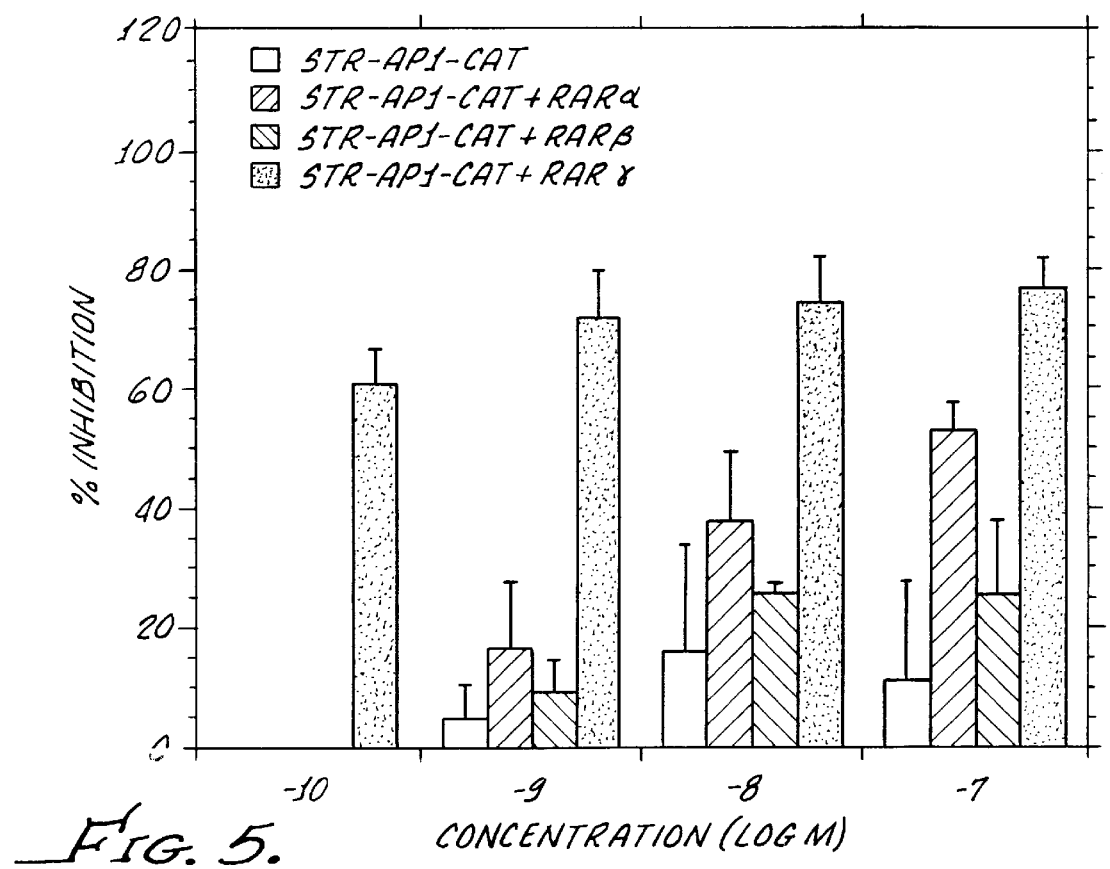
FIG. 5 is a graph showing the effect of varying concentrations of 4-[[5,6,7,8-tetrahydro-5(RS)-(2'(RS)-tetrahydropyranyloxy)-8,8-dimethylnaphth-3-yl]ethynyl] benzoic acid (compound 13 AGN 192509) in the retinoid-mediated AP1 antagonism assay.
Figure 6:
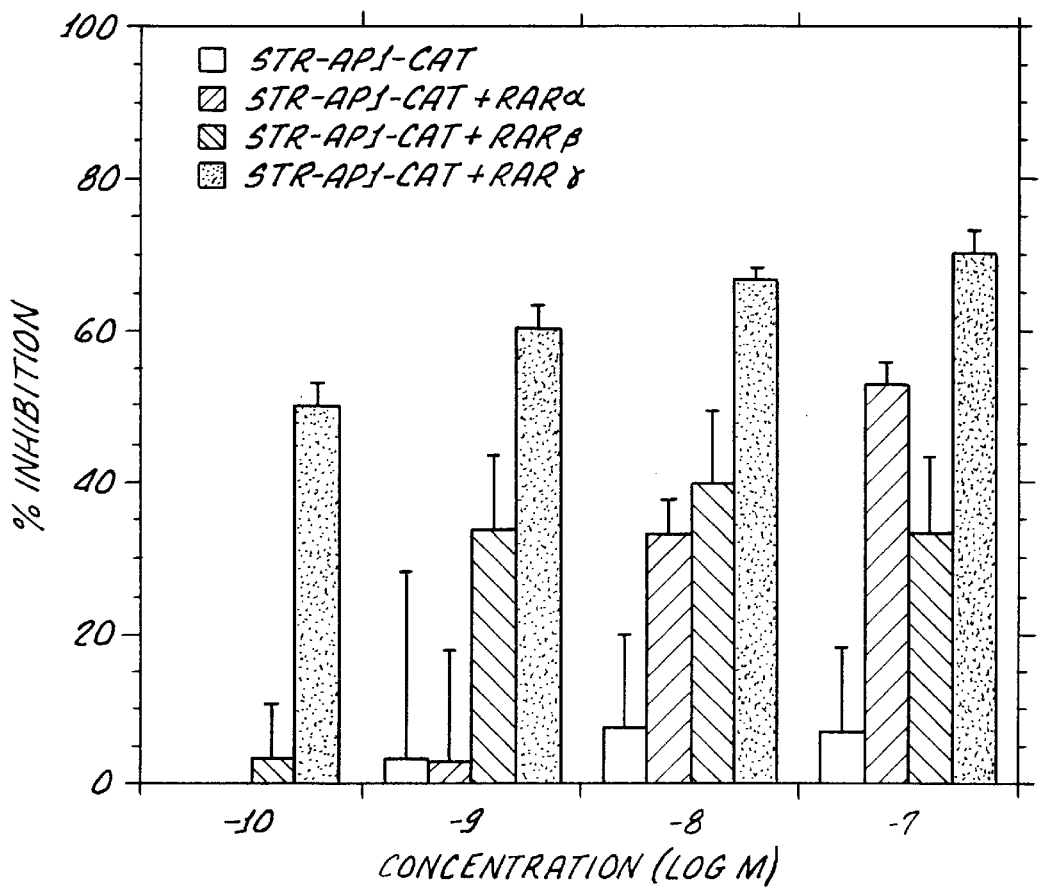
FIG. 6 is a graph showing the effect of varying concentrations of 4-[[5,6,7,8-tetrahydro-5(RS)-(2'(SR)-tetrahydropyranyloxy)-8,8-dimethylnaphth-3-yl]ethynyl] benzoic acid (Compound 14 AGN 192508) in the retinoid-mediated AP1 antagonism assay.

It has been discovered in accordance with the present invention that the beneficial therapeutic and undesired toxic or side-effects of certain retinoid-like compounds can be pharmacologically separated in a practical sense, so that administration of pharmaceutical compositions containing such compounds to mammals, including humans, for therapeutic purposes results in beneficial therapeutic activity with significantly reduced side effects or toxicity.

More specifically, retinoid compounds are designed and discovered in accordance with the present invention which inhibit expression of gene promoted by the AP1 protein through binding as a ligand to all three RAR receptor subtypes (RARα, RARβ and RARΓ). The resulting retinoid ligand-RAR complex interacts with the AP1 protein in such a manner that the AP1 protein promoted gene expression is inhibited or suppressed. The same compounds, designed or discovered in accordance with the present invention, however are specific or selective in their ability to induce gene expression through the RARβ receptor, in preferance over RARα and RARΓ receptors. Mammalian skin, including human skin, is known to contain only insignificant amounts of RARβ receptors. Therefore, when the compounds designed or discovered in accordance with the present invention are administered to a mammal, including a human, for therapeutic purposes, the beneficial effects of AP1 protein-promoted gene inhibition are attained, and the undesired side effects through transactivation are reduced or minimized. Particularly noteworthy in this regard are the lack of side effects in the skin, because skin irritation and other skin toxicity has been considered one of the major disadvantages of conventional therapy with retinoids. The compounds designed or selected in accordance with the present invention have the desired therapeutic effect in the skin because the AP1 protein inhibition occurs through all three RAR receptor subtypes, but substantially lack skin toxicity, because they transactivate only through the RARβ receptor which is practically not present in the skin.

The ability of a "retinoid" compound or ligand to meet the above-described criteria and to be useful in the methods in accordance with the present invention is assayed and demonstrated in the following manner. First, a transactivation assay employing chimeric RARα, RARβ or RARΓ binding regions attached to an estrogen-response-element-chloramphenicol acetyl transferase-construct (ERE-CAT) is used to measure the ability of the test compound or ligand to trigger expression of a synthetic gene containing RARE in its promoter region. This assay is hereinafter referred to as the chimeric receptor transactivation assay which is explained and described in detail as follows.

Chimeric Receptor Transactivation Assay

The assay is performed substantially as reported by Feigner P. L. and Holm M. (1989) Focus, 11, 2 and is based on the following principles, the description of which is followed by specific instructions how to perform the assay.

Retinoic acid receptors are a member of the steroid/thyroid receptor super family and they contain domains which are interchangeable within individual receptors. Thus, plasmids for chimeric retinoid receptors containing estrogen DNA binding domain and estrogen response element chloramphenicol acetyl-transferase enzyme are constructed and are grown in specific cultured bacteria. These plasmids respectively code for chimeric RARα, RARβ, RARΓ, and if desired for testing RXRα, receptor proteins, and for the chloramphenicol acetyl A transferase (CAT) enzyme protein. The bacteria with these plasmids are obtainable in accordance with the procedure set forth in the article titled "Nuclear Retinoic Acid Receptors: Cloning, Analysis, and Function", M. Pfahl et al., Methods in Enzymology 189, p256–270 (1990) which is incorporated herein by reference. The detailed procedure how to isolate the DNA plasmids from the respective bacteria is also set forth below in detail, in the form of specific instructions under the title "Supercoiled Plasmid Isolation".

Thus, in accordance with the test procedure, DNA plasmid which codes for one of the chimeric RARα, RARβ, RARΓ, and if desired for RXRα receptor proteins is transfected into cultures of HeLa cells. It is for this purpose that HeLa cells are grown in a medium during the first day of the assay detailed below as the "Cationic Liposome Mediated Transfection Assay". In the transfection procedure, which is performed during the second day of the transfection assay, the DNA plasmid coding for the CAT enzyme is also added to each cell culture, in addition to the respective chimeric RARα, or RARβ etc. coding plasmid. As is known and will be readily understood by those skilled in the art, especially in view of the above-cited M. Pfahl et al. article, chimeric retinoid receptors involved in this assay include a ligand binding domain which recognizes and binds specific agonist molecules, such as retinoic acid and analogs. These chimeric protein receptors (which were constructed in accordance with the teachings of the M. Pfahl et al. article) also contain a DNA binding domain, which is capable of binding to the "estrogen response element" (a DNA fragment) attached to the DNA plasmid coding for the CAT enzyme. The nature of the interaction is such, that only if an agonist (such as retinoic acid or analog) is bound to the ligand binding domain of the respective RARα, RARβ, etc. receptor, only then is the receptor bound through its DNA-binding domain to the estrogen response element of the estrogen-response-element-chloramphenicol-acetyl transferase-construct (ERE-CAT). In other words, through multiple interactions, CAT enzyme is produced by the HeLa cell in this assay only if an appropriate agonist ligand binds to the ligand binding site of the respective retinoid receptor.

The estrogen response-element-chloramphenicol acetyltransferase construct (ERE-CAT) is itself obtained in accordance with the procedure described in the article Ryssel G. U. et al. Cell, Volume 46, pp 1053–1061 (1986), which is incorporated herein by reference. This procedure per se is well known in the art. The specific detailed procedure how to isolate and obtain the estrogen-response-element chloramphenicol-acetyl-transferase-construct (ERE-CAT) from bacteria is described in the procedure titled "Supercoiled Plasmid Isolation".

In addition to the foregoing, Lipofectin (LF) is also added to each cell culture. The purpose of the Lipofectin is to facilitate transport of plasmids through the cell membrane. The Lipofectin used in the procedure is available commercially.

As it will be well understood by those skilled in the art, as a result of transfection with the respective DNA plasmid coding for RARα, or RARβ etc. chimeric receptors and as a result of transfection with the ERA-CAT (which codes for the CAT enzyme as described above), the aforementioned plasmids are incorporated into the HeLa cells cultured in the assay. The retinoid receptor plasmids undergo transcription (into m-RNA) and subsequent translation into the corresponding chimeric receptor protein. Therefore, the Hela cell cultures obtained in this manner produce the respective RARα, RARβ, RARΓ, or RXRα chimeric receptor protein. As a result of transfection with the ERA-CAT, the cell cultures of this assay also contain the genetic information for manufacturing the CAT enzyme. However, as is noted above, the latter genetic information is not transcribed, and the CAT enzyme is not produced by the respective cell cultures of this assay, unless an appropriate agonist compound binds to and activates the respective RARα, RARβ, RARΓ, or RXRα chimeric receptor protein in the cell and this activated agonist-receptor complex binds to the estrogen response element of the ERE-CAT construct.

The assay procedure is continued by adding, on the third day of the assay, an appropriate reference compound and the test compound (agonist or prospective agonist) to the respective HeLa cell culture, preferably in varying concentrations. As a result of this addition, if the test compound is an agonist, it binds to the respective $RAR_\alpha$, $RAR_\beta$, $RAR_\Gamma$, or $RXR_\alpha$ chimeric receptor protein, and consequently the genetic information which codes for the CAT enzyme is transcribed in the cell, whereby CAT enzyme is made by the cell.

After lysis of the cell, which is performed on the fourth day of the below-detailed assay procedure, the activity of CAT enzyme in aliquot portions of the lysate is measured. This is done by incubating the lysate with chloramphenicol and tritium labeled acetyl coenzyme A. As a final measurement, the amount of tritium labelled acetyl chloramphenicol, which is formed in the enzymatic reaction involving the CAT enzyme, is measured in a scintillation counter.

The reference compound is retinoic acid (all trans) for the assays involving the $RAR_\alpha$, $RAR_\beta$, and $RAR_\Gamma$ receptors. The data obtained in the assay are evaluated and expressed as follows. For each test compound and for each subspecies of the RAR receptors a graph (or the mathematical equivalent of a graph) is prepared where the "counts per minute" (cpm) obtained in the scintillation counter measurements are plotted (on the y axis) against the concentration of the test compound. A similar graph (or mathematical equivalent) is prepared for retinoic acid. $EC_{50}$ of the test compound is defined as that concentration of the test compound which provides ½ (50%) of the maximum cpm number (maximum CAT enzyme activity) obtained in the same receptor in the same assay with the reference compound retinoic acid. This is illustrated in the graph of FIG. 1. Test results obtained in this assay in connection with compounds in accordance with the invention, are expressed in $EC_{50}$ numbers.

SUPERCOILED PLASMID ISOLATION

Large Scale 1L Prep

DNA Isolation

1. Place cells on ice for 15 minutes. Harvest the bacterial cells (*E. coli*) by spinning down in 250 ml nalgene tubes at 7 k rpm, 10 minutes at 4° C. using JA14 rotor, Beckman J2-21 M centrifuge. Discard the supernatant.
2. To each cell pellet add 1.0 ml Solution I, vortex to resuspend the pellet. Transfer the 1.0 ml of cells from one bottle to another. Transfer this to a 50 ml Oakridge tube. Use 4 ml of Solution I and wash the bottles again transferring from one bottle to the next. Transfer this also into the Oakridge tube. Using a pipet bring up the total volume to 16 ml with Solution I and mix the solution. Transfer 8 ml to a second Oakridge tube. Store at room temperature for 5 minutes.

Solution I 50 mM glucose, 25 mM Tris-Cl pH8, 10 mM EDTA pH8

3. Add to each tube 18 ml of freshly prepared Solution II. Mix contents gently by inverting the tube several times. Store on ice for 10 minutes. After this time the liquid should be clear with no aggregates. (If there are clumps, then the cells were not resuspended well enough previously.)

Solution II

1% sodium dodecylsulfate (SDS), 0.2N NaOH (4 ml 10% SDS, 0.8 ml 10N NaOH, 35.2 ml water)

4. Add 12 ml, (or as much as will fit) of ice-cold Solution III. Mix the contents of tube by inverting it sharply several times. A white flocculent precipitate should appear. Store on ice for 10 minutes.

Solution III

Prepare as follows: to 60 ml 5M potassium acetate, add 11.5 ml of glacial acetic acid and 28.5 ml water.

5. Centrifuge at 4° C. in a Beckman J2-21M centrifuge, JA20 rotor, 17 k rpm for 30 minutes.

6. Pipet approximately 12 ml of supernatant from the Oakridge tubes into 6 baked Corex tubes. Add 0.6 volumes of isopropanol (7.2 ml) mix by inversion and store at room temperature for 15 minutes to precipitate DNA.
7. Warm Beckman centrifuge by spinning JA20 rotor at 14 k rpm for 15 minutes at 20° C.
8. Pellet DNA at 20° C. in the J2-21M centrifuge, JA20 rotor at 10.5 k rpm for 30 minutes (use adapters for corex tubes).
9. Pour off supernatant, dry inside of tube with pasteur pipet on a vacuum flask.
10. Dry in vacuum dessicator for 10 minutes (longer drying time will make it hard to dissolve pellet).

Purification of Plasmid DNA by Centrifugation to Equilibrium in CsCl Density Gradients 11. Dissolve pellet by adding 1 ml TE (10 mM Tris-Cl pH 8, 1 mM EDTA pH8) to each corex tube. Place tubes in 37° C. water bath to help pellets to dissolve faster (15–30 minutes).
12. Transfer liquid from like batch into one tube. Bring volume to 8.5 ml with TE.
13. Add 100 µl RNase, DNase free (2 U/µl, source Boehringer Mannheim Biochemical (BMB)).
14. Add 400 µl of 10 mg/ml Ethidium Bromide.
15. Add 9.0 g CsCl and mix using a pasteur pipet.
16. Add solution to two 13×51 mm Beckman polyallomer quick-seal centrifuge tubes.
17. Spin at 50 k rpm for 12 hours in Beckman ultracentrifuge, VTi65.2 rotor, 20° C.
18. After ultracentrifugation, two bands of DNA should be visible. The upper band consists of linear bacterial DNA and nicked circular plasmid DNA. The lower band consists of closed circular plasmid DNA. Only the lower CsCl-banded DNA is removed from the tube with a 3-ml syringe fitted to an 21-gauge needle (Needle is inserted into the side of the tube and 1.5–2 ml is removed).
19. Preparation for second CsCl centrifugation:
    (9 ml—vol 1st CsCl band)—number g CsCl
    (9 ml—vol 1st band—100 µl 10 mg/ml Ethidium Bromide—50 µl RNase)—ml TE pH 8.0
    Combine 1st band, TE, CsCl, RNase and EtBr.
20. Add solution to 2 quick-seal tubes.
21. Spin at 50 k for 12 hours or 60 k rpm for 4 hours in ultracentrifuge, VTi65.2 rotor, 20° C.
22. Remove twice CsCl-banded DNA (lower band only) to a 5 ml Falcon snap tube (as in step 18).

Extraction of Ethidium Bromide

23. Under fume hood add an equal volume isoamyl alcohol, vortex, spin at room temperature at 1500 rpm in Beckman TJ-6 centrifuge for 3 minutes.
24. Transfer bottom aqueous layer to fresh tube. Repeat 3–4 times or until aqueous layer is clear (no pink color).
25. Transfer clear aqueous layer to Spectra/Por 3 dialysis tubing, mwco 3500. (Tie a knot in the bottom of tubing before clamping dialysis tubing.) Add liquid using a pasteur pipet. Clamp top or dialysis tubing. Using a rubber band suspend tubing in 2.8 L TE (28 ml 1M Tris-Cl, pH8, 5.6 ml 0.500M EDTA, pH8). Always handle dialysis tubing carefully, with gloves.
26. Dialyze aqueous phase against several changes of 2.8 L TE pH8 (1× 2–4 hours, overnight and 1× 2–4 hours the next day).
27. In the tissue culture hood transfer the dialyzed DNA into sterile microcentrifuge tubes. Label tubes and store at −20° C.

Cationic Liposome-Mediated Transfection

Reference: Felgner, P. L., and Holm, M. (1989) Focus 11, 2.

Use Sterile Technique Throughout

Grow up HeLa or CV-1 cells in T-125 culture flask. Cells are passed twice a week usually on Monday and Friday (0.5 ml cells into 15 ml medium)

DAY 1: Plating Cells

1. Trypsinize and collect cells from T-162 cm² culture flask. Count cells using a hemocytometer. Usually, this amount of cells is enough for sixteen 12-well plates.
2. Based on the cell number, dilute cells in medium (D-MEM low glucose, 10% fetal bovine serum (FBS), 2 mM Glu) to a concentration of 60,000 cells per well.

Example Cell Calculation want 40,000 cells/well and 200 wells have (X) cells/ml therefore, 40,000 cells/well×200 wells–total # ml cells (X) cells/ml needed Using a Nalge 250 ml Filter Unit Receiver add total #ml cells to medium and bring final volume to 200 ml. Mix well by pipetting.

3. Add 1.0 ml of cells per well using a sterile 12.5 ml combitip (setting 4). Shake plates back and forth (do not swirl). Incubate at 37° C. in a humidified 5% $CO_2$ environment overnight. Cells are about 40% confluent prior to transfection.

Transfection: DAY 2 Preparation DNA/Lipofectin Complex

1. Using 50 ml polystyrene tubes prepare Lipofectin (LF) and DNA separately. Determine vol of LF and DNA needed for 2 μg LF/well, 500 ng ERE-CAT DNA /well, 100 ng ER/RAR DNA per well. Determine total volume needed for experiment. (DNA concentration will vary between each plasmid prep and the following calculations will need to be adjusted accordingly.)

| DNA (prep date) | μl/well | # wells | vol DNA | Vol |
|---|---|---|---|---|
| Opti-Mem | | | | |
| α | | | | |
| β | | | | |
| τ | | | | |
| X | | | | |
| CAT | | | | |
| LF lot # | μl/well | # wells | μl LF | Vol Opti-Mem |

Separately dilute LF and DNA in Opti-Mem media to a volume of 25 ul×#wells: Vol Opti-Mem 1=(25 ul×#wells)–total vol. DNA or LF.

2. Add the diluted LF to the diluted DNA and swirl tube gently. Let sit room temperature for 10 min.
3. Aspirate off the medium from the wells and wash 2× using 0.5 ml Opti-Mem I (sterile 12.5 ml combitip, setting 2).
4. Add the DNA/LF complex to vol of Opti-Mem: (450 μl×# wells). Invert tube to mix. Using a sterile 12.5 ml combitip (setting 2) add 500 μl to each well. Shake plates back and forth to mix, do not swirl.
5. Incubate the cells for 6 hours at 37° C. in a humidified 5% $CO_2$ incubator.
6. After 6 hours add 0.5 ml medium to each well (D-MEM low glucose, 20% FBS charcoal treated, 2 mM Glu) Use 12.5 combitip setting 2 and place back in the incubator.

DAY 3: Drug Addition 1. 18 hours after the start of transfection add retinoids in triplicate (10 μl) using a sterile 0.5 ml combitip (setting 1) and incubate for 20–24 hours at 37° C. in a humidified 5% $CO_2$ environment.

DRUG DILUTIONS $$\frac{\text{weight (g)}}{\text{ACETONE} \cdot \text{mol. wt (g/mol)}} \times \frac{1}{.005 \text{ mol/L}} \times \frac{100 \text{ ml}}{L} = \underline{\quad} \text{ml}$$

Example

Retinoids are dissolved in acetone to a conc. of 5 mM and further diluted to 1 mM in EtOH. If retinoids do not go into solution place tube in hot water for 5 seconds followed by vigorous vortexing. Each experiment may have a different dilution scheme. For 2 concentrations per order of magnitude use a 3.16-fold dilution as follows: To labeled sterile 12×75 mm tubes (Falcon 2063) add 1080 ul of 100% EtOH. Using the 1 mM solution transfer 500 ul to the next tube (316 μM). Vortex and repeat the transfer to the next tube down the line. Some retinoids are light sensitive, especially RA and 13-cis RA, and should be used with a red or very dim light. Log in the amount of compound used.

EXAMPLE

| Drug Dilution | Vol add to well | Final: -log [conc.] |
|---|---|---|
| 5 mM (initial) | | |
| 1 mM | 10 | 5.0 |
| 316 μM | 10 | 5.5 |
| 100 μM | 10 | 6.0 |
| 31.6 μM | 10 | 6.5 |
| 10 μM | 10 | 7.0 |
| 3.16 μM | 10 | 7.5 |
| 1 μM | 10 | 8.0 |
| 316 nM | 10 | 8.5 |
| 100 nM | 10 | 9.0 |
| 31.6 nM | 10 | 9.5 |
| 10 nM | 10 | 10.0 |
| 3.16 nM | 10 | 10.5 |
| 1.0 nM | 10 | 11.0 |

Day 4 Mixed Phase Cat Assay

1. Wash cells in 12 mm wells once with 0.50 ml 1× PBS (no Ca/Mg).
2. Using a 5 ml combipipet (setting 1) add 100 μl of a ice cold 1% Triton, 1 mM Tris-Cl pH7.8, 2 mM EDTA pH8, DNase I. Prepared as follows:

| LYSIS BUFFER (hypotonic buffer) |
|---|
| 2.0 mg DNase I (Sigma) |
| 4.925 ml water |
| 50.0 μl 100% Triton X-100 (BMB Lot # |
| 5.0 μl 1M Tris—Cl pH 7.8 |
| 20.0 μl 0.5M EDTA pH 8 |
| 5.0 ml |

3. Place on ice for 60 minutes. Agitate occasionally.
4. Transfer 50 μl lysate from 3 wells at a time using titertrek multichannel pipet with tips attached to channels #1, #3, #6 to 96 U-bottom well (Costar). Place (unused lysate) plates at −20° C.
5. Using a 1.25 ml combipipet (setting 1) add 50 μl premix per well, gently shake plates and incubate 37° C. for 2 hours.

| Vol. per Blank | Vol per reaction X__ (# assays) = total vol. |
|---|---|
| 47.0 | 27.0 µl buffer I (250 mM Tris—Cl pH 7.8, 5 mM EDTA (Date: |
| 1.5 | 1.5 µl 1 mM HCl |
| *** | 20.0 µl 5 mM Chloramphenicol (make fresh in buffer I) Lot # |
| 0.75 | 0.75 µl 4 mM Acetyl CoA in water (make fresh) Sigma Lot # |
| 0.80 | 0.80 µl 3H—Acetyl CoA (New England Nuclear) # NET-290L, 200 mCi/mmol) |

6. Using a titertrek multichannel pipet add 100 µl of 7M Urea into each reaction well to quench the reaction. Do six at a time (Urea-Mallincrokt AR)

7. Using a titertrek multichannel pipet transfer 200 µl reaction mixture into a 5 ml plastic scintillation vial (Research Products International #125514). Do three reactions at a time. (Urea-Mallincrokt AR)

8. Add 1 ml 0.8% PPO/Toluene (3.2 g PPO/4 L Toluene) Vortex vigorously for 5 seconds and allow the phases to separate for 15 minutes. Count cpm for 2.0 min-Beckman LS 3801.

Toluene-Mallinckrodt ScintillAR
PPO=2,5 Diphenyloxazole-RPI Lot #A3071

Alternatively, another assay, known as the holoreceptor transactivation assay can also be used for measuring the ability of the test compound or ligand to trigger expression of the genes containing RARs in their promoter regions. This assay is based on principles similar to the chimeric receptor transactivation assay described above, and is described below.

Holoreceptor Transactivation Assay

CV1 cells (5,000 cells/well) were transfected with an RAR reporter plasmid ▲MTV-TREp-LUC (50 ng) along with one of the RAR expression vectors (10 ng) in an automated 96-well format by the calcium phosphate procedure of Heyman et al. Cell 68, 397–406. (8). For RXR transactivation assays, an RXR-responsive reporter plasmid CRBP II-TK-LUC (50 ng) along with one of the RXR expression vectors (10 ng) was used substantially as described by Heyman et al. above, and Allegretto et al. J. Biol. Chem. 268, 26625–26633. (8, 9). RXR-reporter contained DRI elements from human CRBP II promoter (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. (8, 9). The results obtained in this assay in connection with exemplary compounds in accordance with the present invention are also expressed in $EC_{50}$ numbers, in analogy to the results in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York are expressly incorporated herein by reference.

Another assay used to determine the ability of a potential ligand (test compound) to meet the criteria of the present invention, is the retinoid-mediated AP1 antagonism assay which is described as follows.

Retinoid-Mediated AP1 Antagonism Assay

The anti-AP1 properties of retinoids are determined by measuring their ability to inhibit AP1-dependent gene expression in HeLa cells by transiently contransfecting them with a reporter gene and a receptor expression vector. Since the DNA binding domain of the RARs is involved in the inhibition of AP1 dependent gene expression (Schule. et al. Proc. Natl. Acad. Sci. U.S.A., 88:6092–6096, 1991), holoreceptors of RARs (α, β, and Γ) are used in transfection assays to quantitate the relative potency of retinoids in antagonism of AP1-dependent gene expression.

Recombinant Plasmids

The expression vectors for RARs (α, β, and Γ) have been described (Allegretto. et al., J. Biol. Chem. 268:26625–26633, 1993). AP1-reporter plasmid construct Str-AP1-CAT was prepared by cloning −84 to +1 base pairs of rat stromelysin-1 promoter (Matrisian et al., 6:1679–1686, 1986) in Hind III-Bam HI sites of pBLCAT3 (Luckow et al, Nucl. Acids Res. 15:5490, 1987). This sequence of stromelysin-1 promoter contains an AP1 motif as its sole enhancer element (Nicholson, et al., EMBO J. 9:4443–4454, 1990). The promoter sequence was prepared by annealing two synthetic oligonucleotides 5'AGAAGCTT ATG GAA GCA ATT ATG AGT CAG TTT GCG GGT GAC TCT GCA AAT ACT GCC ACT CTA TAA AAG TTG GGC TCA GAA AGG TGG ACC TCG A GGATCCAG3' (SEQ ID NO.1) and 5'-CT GGATCC TCG AGG TCC ACC TTT CTG AGC CCA ACT TTT ATA GAG TGG CAG TAT TTG CAG AGT CAC CCG CAA ACT GAC TCA TAA TTG CTT CCA T AAGCTT CT-3' (SEQ ID No. 2) containing Hind III and Bam HI restriction sites at their ends.

Transfection of Cells and CAT Assays

For retinoid-mediated AP1-antagonism assay, HeLa cells grown in Dulbecco's modified Eagle's medium (DMEM) containing 10% fetal bovine serum (FBS, Life Technologies, Inc.) are transfected using the cationic liposome-mediated transfection procedure (Felgner, et al., Focus, 11:2, 1989). Cells are plated 18 hours before transfection at about 40% confluence (40,000–50,000 cells/well) in a 12-well tissue culture plate (Costar, Massachusettes). Cells are transfected with 1 µg of reporter construct Str-AP1-CAT and 0.2 µg of human RAR α, β or Γ expression vectors, along with 2 µg of Lipofectamine (Life Technologies, Inc.) for each well in a total volume of 500 µl. DNA/Lipofectamine complexes obtained by mixing 2 µg Lipofectamine/well, 1 µg Str-AP1-CAT/well, and 0.2 µg RAR expression vector in a 50 ml polystyrene tube are incubated with HeLa cells. DNA is precipitated with Lipofectamine for 30 minutes at room temperature before transfer to cells. Five hours post-transfection, 500 µl of DMEM containing 20% charcoal treated FBS (Gemini Bioproducts, Inc. California) is added. All the transfections are performed in triplicate. Test retinoids (at $10^{-10}$ to $10^{-7}$ M concentrations) are added 18 hours post-transfection and 6 hours later the cells are treated with 12-O-tetradecanoyl phorbyl-13-acetate (TPA) to induce AP1 activity. Retinoids are dissolved in acetone to a concentration of 5 mM and further diluted from this stock solution using ethanol. The next day after washing with phosphate buffered saline without calcium and magnesium (Life Technologies, Inc.), the cells are harvested and lysed for 60 min with occasional agitation using a hypotonic buffer (100 µl/well) containing Dnase I, Triton X-100, Tris-HCl and EDTA. CAT activity is assayed in 50 µl of the lysed cell extract using [$^3$H]acetyl CoA (DuPont NEN) in a 96-well U-bottom plate (Costar, Massachusettes). The CAT activity is quantified by counting the amount of $^3$H-acetylated forms of chloramphenicol using a liquid scintillation counter.

The results of this assay can be expressed in percentage of inhibition of TPA induced Str-AP1-CAT by RARs and varying concentrations of a test compound. The result of this assay for a number of examplary compounds in accordance with the invention are shown in graphs appended to this application as drawing figures.

The Schule, et al. Proc. Natl. Acad. Sci. U.S.A., 88:6092–6096, 1991, Matrisian et al., 6:1679–1686, 1986), Luckow et al, Nucl. Acids Res. 15:5490, 1987), Nicholson, et al., EMBO J. 9:4443–4454, 1990), and Felgner et al., Focus, 11:2, 1989) articles are hereby expressly incorporated by reference.

Another assay in which the ability of compounds in accordance with the present invention to inhibit AP1 protein promoted gene expression is tested and determined is described below. It has been observed that compounds designed or discovered in accordance with the present invention bind to all three RAR receptor subtypes ($\alpha$, $\beta$ and $\Gamma$), and remove the AP1 protein from its ability to promote gene expression, even though the same compound transactivates specifically or selectively only through the RAR$\beta$ subtype.

In Vitro RAR Binding Assay

For in vitro RAR binding experiments, baculovirus/Sf21 insect cell system was used to express human RAR$\alpha$, -$\beta$, and -$\Gamma$ as described Allegretto et al. J. Biol. Chem. 268, 26625–26633 (9). Suspension-grown Sf21 cells were infected with the recombinant viruses at a multiplicity of infection of 2 for 48 hours, followed by disruption of the infected cells in 10 mM Tris, pH 7.6, 5 mM dithiothreitol, 2 mM EDTA, 1 mM phenylmethylsulfonyl fluoride, and 0.4 M KCl as described Heyman et al. Cell 68, 397–406, and Alegretto et al. cited above. (8, 9). The binding assay contained 5–20 $\mu$g of extract protein along with [$^3$H]all-trans-retinoic acid (5 nM) and varying concentrations (0–10$^{-5}$M) of competing ligand in a 250 $\mu$l reaction. The binding assays were performed substantially as described previously in Heyman et al. cited above, and Alegretto et al. cited above (8, 9). The results of this assay are expressed, as customary in the art, in KD$_{50}$ numbers.

It follows from the foregoing description that compounds which can be used in the methods of selective suppression of AP1-promoted gene expression, and therefore as therapeutic agents of reduced skin toxicity, show significant binding in the in vitro RAR binding assay substantially to all three RAR subtypes, and inhibit AP1 protein promoted gene expression in the retinoid-mediated AP1 antagonism assay. These compounds however, show substantial transactivation in the chimeric receptor transactivation assay or in the holoreceptor transactivation assay only through the RAR$\beta$ receptor subtype. In other words, in the transactivation assays, the compounds do not show significant transactivation through RAR$\beta$ and RAR$\Gamma$ receptors. In as much as the compounds do show some transactivation through RAR$\beta$ receptors (which are not present in substantial amount in the skin), it is generally speaking a criterion for the compounds used in the invention that they should be at least approximately 20 times less active through the RAR$\alpha$ and RAR$\Gamma$ receptors than through the RAR$\beta$ receptors.

Accordingly, the foregoing assays provide a method for selecting retinoid compounds as potential useful drugs having reduced skin toxicity. The drugs so selected or designed to meet the criteria of the invention, are then utilized for treatment in combination with conventional pharmaceutical excipients.

In determining appropriate formulations one skilled in the art will consider that the compounds utilized in accordance with this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

ASSAY RESULTS

Tables 2 and 3 and the graphs of FIGS. 2–6 show the results of some of the above described assays with exemplary compounds, in accordance with the invention. For the purposes of biological testing the compounds are assigned arbitrary designation numbers (AGN numbers) which are shown in the drawing figures. To facilitate comparison with the numbering of compounds in this application, Table 1 shows the correspondence between the "AGN number" and the "compound number" in this application.

TABLE 1

| Compound # | AGN # |
|---|---|
| 2 | 192156 |
| 7 | 192326 |
| 8 | 192327 |
| 13 | 192509 |
| 14 | 192508 |

TABLE 2

| | $EC_{50}$ (nanomolar) | | |
|---|---|---|---|
| Compound # | RARα | RARβ | RARΓ |
| Chimeric Receptor Transactivation Assay | | | |
| 2 | 0.0 | 47.0 | 0.0 |
| 7 | 2520 | 2.63 | 303 |
| 8 | 0.0 | 8.24 | 1590 |
| Holoreceptor Transactivation Assay | | | |
| 13 | 0.0 | 69.0 | 0.0 |
| 14 | 0.0 | 90 | 0.0 |

0.0 in Table 2 indicates a value greater than 1000 nM

TABLE 3

| | In Vitro RAR Binding Assay | | |
|---|---|---|---|
| | $KD_{50}$ (nanomolar) | | |
| Compound # | RARα | RARβ | RARΓ |
| 2 | 1178 | 295 | 509 |
| 7 | 95 | 108 | 103 |
| 8 | 505 | 468 | 391 |
| 13 | 129 | 17 | 63 |
| 14 | 171 | 75 | 104 |

As can be seen in Table 2 the compounds used in the methods of the invention are substantially inactive to transactivate, (trigger expression of genes which have RAREs in their promoter region) through RARα and RARΓ receptors. However, as Table 3 indicates, these compounds are still capable of binding with approximately the same strength to all three of the RARα, RARβ and RARΓ receptors. The latter is an indication of their ability to repress AP1 protein promoted gene expression. FIGS. 2–6 of the appended drawing figures show the results obtained with varying concentrations of the exemplary compounds 2, 7, 8, 13, and 14 in the retinoid mediated AP1 antagonism assay. These data also show, that even though the compounds do not transactivate significantly through the RARα and RARΓ receptors, they inhibit AP1 promoted gene expression through all three RAR receptor subtypes.

DESCRIPTION AND PREPARATION OF COMPOUNDS IN ACCORDANCE WITH THE PRESENT INVENTION

Compounds which, in accordance with the present invention are suitable for use in the method of AP1-promoted gene suppression and the resulting therapeutic applications, have the structure shown by Formula 1 and Formula 2, where X is N or CH, R is H or lower alkyl of 1 to 6 carbons; in Formula 1 the tetrahydropyranyloxy and the t-butyl groups are attached either to the 3 or the 4 position of the phenyl ring, and where the wavy lines represent a bond which is of either stereo-isomeric configuration that is possible for that bond.

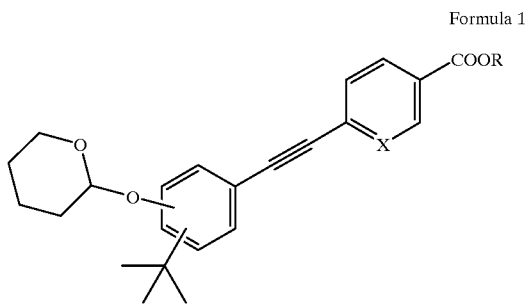

Formula 1

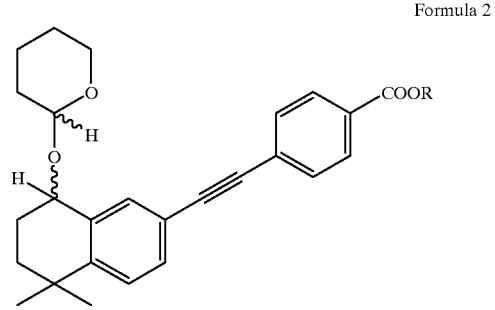

Formula 2

In the description of the compounds the term alkyl refers to and covers any and all groups which are known as normal alkyl, branched-chain alkyl and cycloalkyl. Lower alkyl means the above-defined broad definition of alkyl groups having 1 to 6 carbons, and as applicable, 3 to 6 carbons for branch chained and cycloalkyl groups. The term "ester" as used here refers to and covers any compound falling within the definition of that term as classically used in organic chemistry. A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds utilized in accordance with the present invention may contain one (and may contain more than one) chiral center and therefore exist in enantiomeric and diastereomeric forms. Unless otherwise stated, the scope of the present invention is intended to cover all such isomers per se, as well as mixtures of diastereomers and racemic mixtures of enantiomers (optical isomers) as well.

Referring again to the compounds of Formula 1 and Formula 2, the R group is even more preferably H, or lower alkyl of 1 to 3 carbons.

Specific examples of compounds used in the methods of the present invention are disclosed in Table 4 with specific reference to Formula 1 and Formula 2.

TABLE 4

| Compound # | Formula # | Position of THP[1] on phenyl ring[2] | position of t-butyl group | R | X |
|---|---|---|---|---|---|
| 2 | 1 | 4 | 3 | H | CH |
| 7 | 1 | 3 | 4 | H | CH |
| 8 | 1 | 3 | 4 | H | N |
| 13 | 2 | — | — | H[3] | — |
| 14 | 2 | — | — | H[4] | — |

[1]THP stands for tetrahydropyranyloxy
[2]the ethynyl substituent occupies position "1" on the phenyl ring for the purposes of numbering in this table
[3]Assymetric centers of the (5RS) and 2'-(RS) configuration
[4]Assymetric centers of the 5-(RS) and 2'-(SR) configuration The compounds of Formula 1 and Formula 2 can be made by the synthetic chemical pathways illustrated here. The synthetic chemist will readily appreciate that the conditions set out here are specific embodiments which can be generalized to any and all of the compounds represented by these formulas.

tuted bromophenols of Formula 4. The bromophenols of Formula 3 are commercially available thereby rendering the compounds of Formula 4 readily accessible to one of ordinary skill in the art as commercially available chemicals and/or through use of such Fridel Crafts alkylation (and the like) reactions which are well known in the art.

The compounds of Formula 4 are then reacted with 3,4-dihydro-2H-pyran (DHP) to provide the 2-tetrahydropyranoxy bromobenzenes of Formula 5. The latter reaction is typically conducted in an inert aprotic solvent, such as dichlomethane, under mildly acidic conditions, such as in the presence of pyridinium p-toluenesulfonate. The 2-tetrahydropyranoxy bromobenzenes of Formula 5 are thereafter reacted with trimethylsilylacetylene to provide the 2-tetrahydropyranoxy trimethylsilylethynylbenzenes of Formula 6. The reaction with trimethylsilylacetylene is typically conducted at moderate heat (approximately 55° C.) in the presence of cuprous iodide, a suitable catalyst, typically having the formula $Pd(PPh_3)_2Cl_2$, an acid acceptor (such as triethylamine) under an inert gas (argon) atmosphere. The 2-tetrahydropyranoxy trimethylsilylethynylbenzenes of Formula 6 are then reacted with base (potassium hydroxide or potassium carbonate) in an alcoholic solvent, such as methanol, to provide the tetrahydropyranoxy ethynylbenzenes of Formula 7. The ethynyl compounds of Formula 7 are preferably coupled directly with the aromatic or het-

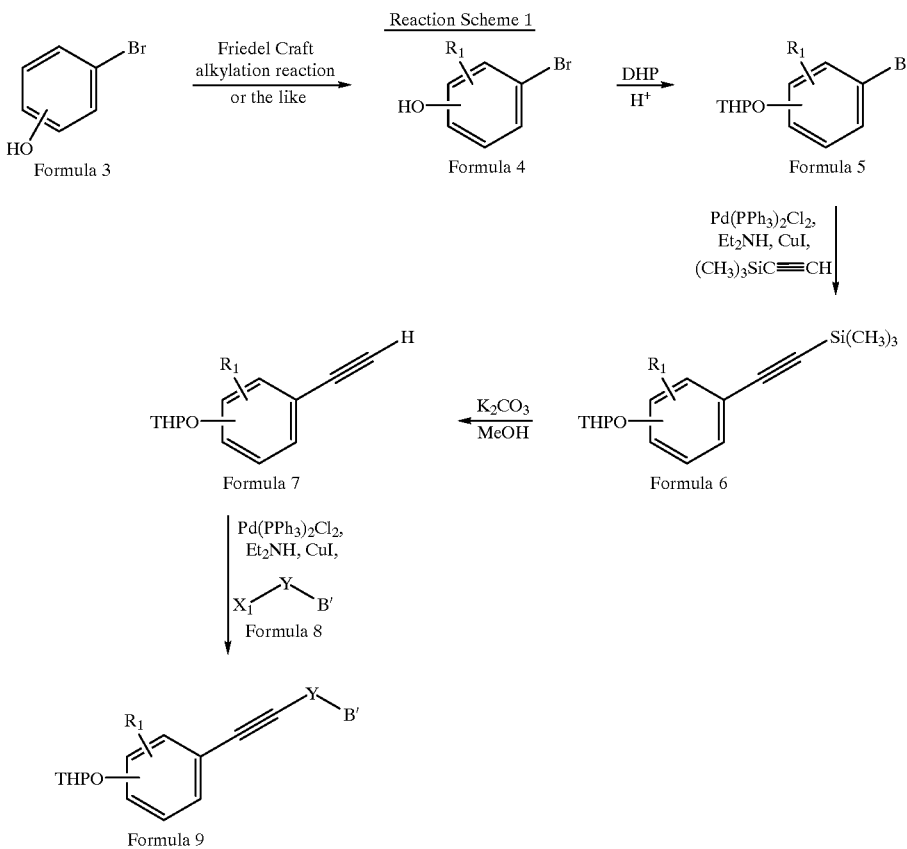

Reaction Scheme 1

Referring now specifically to Reaction Scheme 1, the t-butyl substituent group (indicated in the scheme as $R_1$) is introduced by a Friedel-Crafts (or the like) reaction into the bromophenol compound of Formula 3, to yield the substieroaromatic reagent $X_1$—Y—B' (Formula 8) in the presence of cuprous iodide, a suitable catalyst, typically $Pd(PPh_3)_2Cl_2$, an acid acceptor, such as diethylamine, under inert gas (argon) atmosphere. The symbol $X_1$ in Formula 8 represents a halogen, preferably chloro or iodo; the symbol Y represents the phenyl or pyridyl ring shown in Formula 1; and B' represents the carboxylic acid or carboxylic acid ester shown in Formula 1, or a synthetic precursor of the same from which the carboxylic acid or carboxylic acid ester group can be readily obtained by synthetic steps well known by the practicing organic chemist. Alternatively, a zinc salt (or other suitable metal salt) of the compounds of Formula 7 can be coupled with the reagents of Formula 8 in the presence of Pd(PPh$_3$)$_4$ or similar complex. Generally speaking, coupling between an ethynylbenzene compound or its zinc salt and a halogen substituted aryl or heteroaryl compound, such as the reagent of Formula 8, are described in U.S. Pat. No. 5,264,456, the specification of which is expressly incorporated herein by reference. The compounds of Formula 9 are the compounds of the invention defined by Formula 1, or such derivatives thereof protected in the B' group, from which the protecting group can be readily removed by reactions well known in the art. One such reaction employed for the synthesis of several exemplary compounds of this invention is saponification of an ester group to provide the free carboxylic acid or its salt.

The halogen substituted phenyl or pyridyl compounds of Formula 8 can, generally speaking, be obtained by reactions well known in the art. An example of such compound is ethyl 4-iodobenzoate which is obtainable, for example, by esterification of 4-iodobenzoic acid. Another example is ethyl 6-iodonicotinate which can be obtained by conducting a halogen exchange reaction on 6-chloronicotinic acid, followed by esterification.

accordance with this scheme, a 7-bromo-3,4-dihydro-naphthalen-1(2H)-one of Formula 10 is the starting material. This compound is obtained from ethyl (4-bromophenyl) acetate in a series of reaction steps which are described in detail in the specific embodiments (experimental) section of this application. Thus, in accordance with Reaction Scheme 2 the compound of Formula 10 is reacted with trimethylsilylacetylene to provide 7-trimethylsilylethynyl-3,4-dihydro-naphthalen-1(2H)-one (Formula 11). The reaction with trimethylsilylacetylene is typically conducted under heat (approximately 100° C.) in the presence of cuprous iodide, a suitable catalyst, typically having the formula Pd(PPh$_3$)$_2$Cl$_2$, an acid acceptor (such as diethylamine) under an inert gas (argon) atmosphere. Typical reaction time is approximately 24 hours. The 7-(trimethylsilyl)ethynyl-3,4-dihydro-naphthalen-1(2H)-one of Formula 11 is then reacted with base (potassium hydroxide or potassium carbonate) in an alcoholic solvent, such as methanol, to provide 7-ethynyl-3,4-dihydro-1-naphthalen-1(2H)one of Formula 12. The compound of Formula 12 is then coupled with the aromatic (phenyl) or heteroaromatic (pyridyl) reagent X$_1$—Y—B' (Formula 8, defined as in connection with Scheme 1) in the presence of cuprous iodide, a suitable catalyst, typically Pd(PPh$_3$)$_2$Cl$_2$, an acid acceptor, such as triethylamine, under inert gas (argon) atmosphere. Alternatively, a zinc salt (or other suitable metal salt) of the compound of Formula 12 can be coupled with the reagents of Formula 8 in the presence of Pd(PPh$_3$)$_4$ or similar complex. Typically, the coupling reaction with the reagent X$_1$—Y—B' (Formula 8) is conducted at room or moderately elevated temperature. The 7,8-dihydro-naphthalen-5(6H)-one derivatives of Formula 13

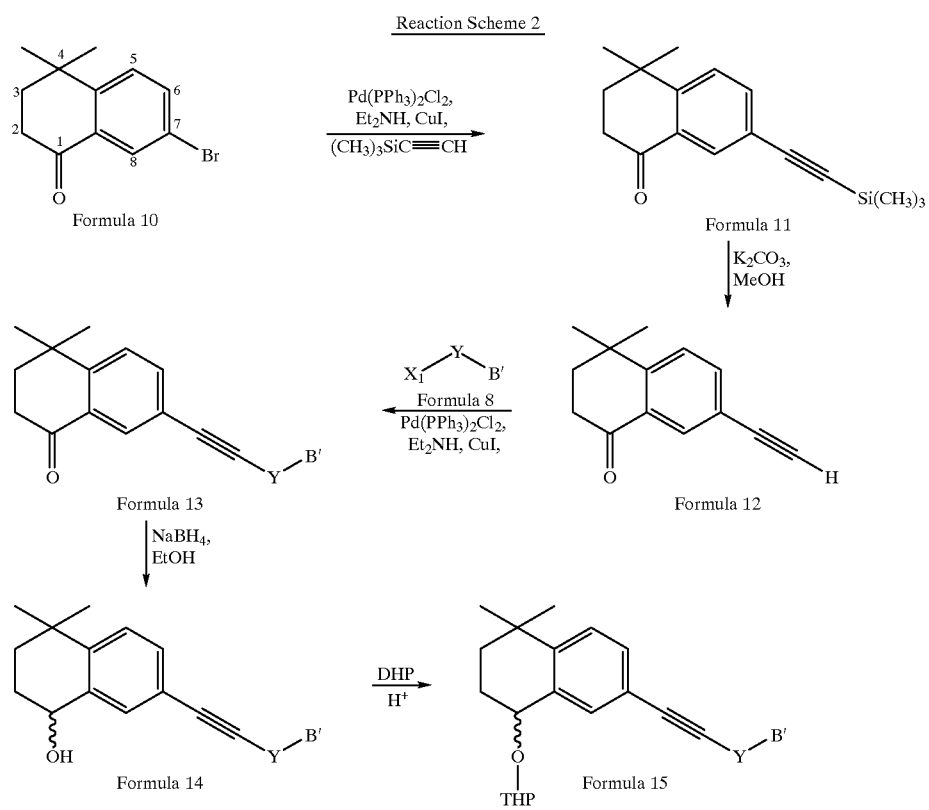

Reaction Scheme 2

Referring now to Reaction Scheme 2 a synthetic route leading to the compounds of Formula 2 is illustrated. In are reduced with a mild reducing agent such as sodium borohydride, to yield the corresponding 5-hydroxy-5,6,7,8- tetrahydronaphthalene derivatives of Formula 14. The compounds of Formula 14 are thereafter reacted with 3,4-dihydro-2H-pyran (DHP) to provide the 2-tetrahydropyranoxy derivatives of Formula 15. The latter reaction is conducted under conditions similar to the conditions described above in connection with Reaction Scheme 1, namely under mildly acidic conditions, such as in the presence of pyridinium p-toluenesulfonate. The diastereomeric tetrahydropyranoxy compounds can be separated by conventional techniques such as chromatography. The compounds of Formula 15 are the compounds of the invention defined by Formula 2, or such derivatives thereof protected in the B' group, from which the protecting group can be readily removed by reactions well known in the art.

Detailed Experimental Procedure of Synthesis, Specific Embodiments

Ethyl 4-iodobenzoate (Compound A)

To a suspension of 24.9 g (100.4 mmol) of 4-iodobenzoic acid in 46.25 g (58.9 ml, 1.0 mol) of ethanol (95%) was added 3.0 ml of conc. sulfuric acid. The resulting mixture was refluxed for 60 minutes, and then distilled until a clear, homogeneous solution was obtained. The solution was allowed to cool to room temperature, partitioned between 250 ml of water and 250 ml of pentane, and the layers were separated. The aqueous phase was washed with 3×100 ml-portions of pentane. All organic phases were combined, washed with brine solution, dried over $MgSO_4$, filtered and concentrated in vacuo to a dark yellow oil. Purification by flash chromatography (silica, 10% ethyl acetate in hexane) yielded the title compound as a clear, light yellow oil. PMR ($CDCl_3$): d 1.39 (3H, t, J=7.2 Hz), 4.37 (2H, q, J=7.2 Hz), 7.73–7.82 (4H, m).

6-Iodonicotinic acid (Compound B)

To 27.97 g (186.6 mmol) of sodium iodide cooled to −78° C. was added 121.77 g (71.6 ml, 952.0 mmol) of hydriodic acid (in 57 wt % aqueous solution). The reaction mixture was allowed to warm slightly with stirring for 5 minutes, and then 30 g (190.4 mmol) of 6-chloronicotinic acid was added. The resulting mixture was allowed to warm to room temperature with stirring and then heated at 120–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1N $NaHSO_3$ solution, and dried in vacuum (3 mm Hg) to give the title compound as a pale yellow solid. PMR (DMSO-$d_6$): d 7.90 (1H, dd, J=8.1, 2 Hz), 7.99 (1H, d, J=8.1 Hz), 8.80 (1H, d, J=2 Hz).

Ethyl 6-iodonicotinate (Compound C)

To a suspension of 23.38 g (94.2 mmol) of 6-iodonicotinic acid in 100 ml of dichloromethane was added a solution of 19.86 g (103.6 mmol) of 1-(3-dimethylaminopropyl)-3-ethylcarbodiimide hydrochloride in 250 ml of dichloromethane. To this suspension was added 12.40 g (15.8 ml, 269.3 mmol) of ethanol (95%) and 1.15 g (9.4 mmol) of 4-dimethylaminopyridine. The resulting solution was then heated at 50° C. in an oil bath for 24.5 hours, concentrated in vacuo, partitioned between 200 ml of water and 250 ml of ethyl ether, and the layers were separated. The aqueous phase was washed with 2×150 ml-portions of ethyl ether. All organic phases were combined, washed once with 75 ml of brine solution, dried over $MgSO_4$, filtered and concentrated in vacuo to yield a yellow solid residue. Purification by flash chromatography (silica, 10% ethyl acetate in hexane) yielded the title compound as a white solid. PMR ($CDCl_3$): d 1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

5-Bromo-2-t-butylphenol (Compound D)

To a solution of 29.46 g (170.3 mmol) of 3-bromophenol (distilled) and 16.41 g (20.9 ml, 221.3 mmol) of t-butanol in 100 ml of carbon tetrachloride was added 20 ml of conc. sulfuric acid. The clear, colorless solution turned a dark magenta color and became hot. The solution was cooled in water (ambient temperature) and allowed to stir at room temperature for 84 hours. The reaction mixture was neutralized with sat. $NaHCO_3$ solution (pH ~7.0), partitioned between 300 ml of water and 500 ml of dichloromethane, and the organic and aqueous layers were separated. The aqueous phase was washed with 2×500 ml-portions of dichloromethane. All organic phases were combined, washed with 400 ml of brine solution, dried over $MgSO_4$, filtered and concentrated in vacuo to a purple oil. Purification by flash chromatography (silica, 5% ethyl acetate in hexane) followed by kugelrohr distillation (85–95° C., 2 mm Hg) yielded the title compound as a clear, slightly yellow oil.

PMR ($CDCl_3$): d 1.37 (9H, s), 4.89 (1H, s), 6.83 (1H, d, J=2.0 Hz), 6.99 (1H, dd, J=8.5, 2.0 Hz), 7.12 (1H, d, J=8.5 Hz).

4-Bromo-2-t-butylphenol (Compound E)

Using the same procedure as for the preparation of 5-bromo-2-t-butylphenol (Compound D), but instead using 50 g (289.0 mmol) of 4-bromophenol, 21.40 g (27.25 ml, 289.0 mmol) of t-butanol and 14 ml of conc. sulfuric acid (added slowly) and 140 ml of distilled carbon tetrachloride, stirred at room temperature for 24 hours produced a dull green-colored solution and a white precipitate. At this time an additional 3.5 ml of conc. sulfuric acid was added and the solution was allowed to stir for 4 days more at room temperature. After aqueous workup, a dark yellow oil was isolated. Purification by flash chromatography (silica, 2% ethyl acetate in hexane) yielded the title compound as a clear, light yellow oil. PMR ($CDCl_3$): d 1.38 (9H, s), 4.79 (1H, s), 6.54 (1H, d, J=8.5 Hz), 7.16 (1H, dd, J=8.5, 2.5 Hz), 7.35 (1H, d, J=2.5 Hz).

4-Bromo-2-t-butyl-1-(2-tetrahydropyranoxy)benzene (Compound H)

To a solution of 18.92 g (82.6 mmol) of 4-bromo-2-t-butylphenol (Compound E) in 110 ml of dichloromethane was added dropwise 10.42 g (11.3 ml, 123.9 mmol) of 3,4-dihydro-2H-pyran. To this clear, colorless solution was added 1.86 g (7.4 mmol) of pyridinium p-toluenesulfonate. The resulting mixture was stirred at room temperature under a blanket of argon for 26.5 hours, partitioned between 250 ml of water and 400 ml of hexane, and the layers were separated. The organic phase was washed with 2×250 ml-portions of water, washed once with 150 ml of brine solution, dried over $MgSO_4$, filtered and concentrated in vacuo to a yellow oil. Purification by flash chromatography (silica, 5% ethyl acetate in hexane) yielded the title compound as a light yellow, crystalline solid. PMR ($CDCl_3$): d 1.39 (9H, s), 1.6–2.1 (6H, m), 3.6–3.7 (1H, m), 3.8–3.9 (1H, m), 5.43 (1H, t, J=2.7 Hz), 7.06 (1H, d, J=8.8 Hz), 7.24 (1H, dd, J=8.8, 2.7 Hz), 7.36 (1H, d, J=2.7 Hz).

5-Bromo-2-t-butyl-1-(2-tetrahydropyranoxy)benzene (Compound I)

Using the same procedure as for the preparation of 4-bromo-2-t-butyl-1-(2-tetrahydropyranoxy)benzene (Compound H), but instead using 8.18 g (35.7 mmol) of 5-bromo-2-t-butylphenol (Compound D), 0.90 g, 3.6 mmol) of pyridinium p-toluenesulfonate and 4.50 g (4.9 ml, 53.6 mmol) of 3,4-dihydro-2H-pyran and 50 ml of dichloromethane stirred at room temperature for 21 hours produced a dark yellow solution. At this time an additional 1.80 g (7.2 mmol) of pyridinium p-toluenesulfonate was added to the solution and it was allowed to stir at room temperature for 19 hours. After aqueous workup a clear, yellow oil was isolated. Purification by flash chromatography (silica, 5% ethyl acetate in hexane) yielded the title compound as a clear, slightly yellow oil. PMR (CDCl$_3$): d 1.38 (9H, s), 1.6–2.1 (6H, m), 3.65–3.75 (1H, m), 3.8–3.95 (1H, m), 5.45 (1H, t, J=2.5 Hz), 7.03 (1H, dd, J=8.4, 2.0 Hz), 7.13 (1H, d, J=8.4 Hz), 7.33 (1H, d, J=2.0 Hz).

2-[[2-t-Butyl-1-(2-tetrahydropyranoxy)]-4-phenyl]acetylene (Compound N)

A sealed tube was purged under a slight vacuum with a stream of argon gas for several minutes. To this tube was added 20 ml of triethylamine (distilled over solid KOH). Under slight vacuum, the solvent was degassed with a stream of argon gas for 2 minutes and then 5 g (16 mmol) of 4-bromo-2-t-butyl-1-(2-tetrahydropyranoxy)benzene (Compound H) and 0.61 g (3.2 mmol) of cuprous iodide (ground to a powder) were added. The resulting yellow mixture was degassed (as described above) for 3.5 minutes. To the degassed mixture was added 2.33 g (3.3 mmol) of bis(triphenyl)phosphine palladium (II) chloride and 15 ml of triethylamine. The reaction mixture was degassed for 5.5 minutes and then 7.71 g (11.1 ml, 78.5 mmol) of trimethylsilyl acetylene was added. The tube was sealed and then heated in an oil bath at 55° C. for 3 days. The solution turned dark brown and a black solid formed. The solid was filtered over celite, washed with approximately 350 ml of ethyl ether and discarded. The filtrate was washed with 3×150 ml-portions of water, washed once with 100 ml of brine solution, dried over K$_2$CO$_3$, filtered and concentrated in vacuo to a dark brown, viscous oil. Purification by flash chromatography (silica, 1% ethyl acetate in hexane) yielded 2-[2-t-butyl-1-(2-tetrahydropyranoxy)-4-phenyl]-1-trimethylsilyl acetylene. The crude TMS-acetylene was dissolved in 35 ml of methanol and 0.16 g (1.2 mmol) of anhydrous potassium carbonate was added to the solution. The solution was allowed to stir at room temperature overnight, concentrated in vacuo, diluted with 35 ml of sat. NaHCO$_3$ solution and allowed to stir at room temperature for 5 minutes. The solution was extracted with 50 ml of dichloromethane and the layers were separated. The aqueous layer was washed with 3×50 ml-portions of dichloromethane. All organic phases were combined, washed once with 100 ml of water, washed once with 50 ml of brine solution, dried over MgSO$_4$, filtered and concentrated in vacuo to yield an orange solid. Purification by flash chromatography (silica, 5% ethyl acetate in hexane) yielded the title compound as a yellow solid. PMR (CDCl$_3$): d 1.40 (9H, s), 1.6–2.1 (6H, m), 2.98 (1H, s), 3.6–3.7 (1H, m), 3.8–3.9 (1H, m), 5.49 (1H, t, J=2.6 Hz), 7.11 (1H, d, J=8.5 Hz), 7.31 (1H, dd, J=8.5, 2.1 Hz), 7.43 (1H, d, J=2.1 Hz).

2-[[2-t-Butyl-1-(2-tetrahydropyranoxy)]-5-phenyl]acetylene (Compound O)

Using the same procedure as for the preparation of 2-[[2-t-butyl-1-(2-tetrahydropyranoxy)]-4-phenyl]acetylene (Compound N), but instead using 10.07 g (32.1 mmol) of 5-bromo-2-t-butyl-1-(2-tetrahydropyranoxy)benzene (Compound I), 1.53 g (8.0 mmol) of cuprous iodide (ground to a powder), 5.64 g (8.0 mmol) of bis(triphenyl)phosphine palladium (II) chloride, 15.79 g (22.7 ml, 160.7 mmol) of trimethylsilyl acetylene and 70 ml of diethylamine (distilled over solid KOH) heated in an oil bath at 55° C. for 43.5 hours produced a brown solution. At this time, an additional 0.78 g (4.1 mmol) of cuprous iodide (ground to a powder), 2.82 g (4.0 mmol) of palladium (II) catalyst and 10.4 ml (73.6 mmol) of TMS-acetylene were added to the mixture. The tube was resealed and heated at 55° C. in an oil bath for 2 days to give a brown oil following aqueous workup. Purification by flash chromatography (pre-absorbed onto silica with chloroform, eluted with 5% ethyl acetate in hexane) yielded 2-[[2-t-butyl-1-(2-tetrahydropyranoxy)]-5-phenyl]-1-trimethylsilyl acetylene. The crude TMS-acetylene was converted into the title compound by using 0.78 g (5.7 mmol) of anhydrous potassium carbonate and 100 ml of methanol to give a brown oil following aqueous workup. Purification by flash chromatography (silica, 3% ethyl acetate in hexane) yielded the title compound as an orange oil. PMR (CDCl$_3$): d 1.40 (9H, s), 1.6–2.1 (6H, m), 3.01 (3H, s), 3.6–3.7 (1H, m), 3.8–3.95 (1H, m), 5.47 (1H, t, J=2.7 Hz), 7.06 (1H, dd, J=8.0, 1.7 Hz), 7.22 (1H, d, J=8.0 Hz), 7.31 (1H, d, J=1.7 Hz).

Ethyl 4-[2-[[2-t-butyl-1-(2-tetrahydropyranoxy)]-4-phenyl]ethyn-1-yl]benzoate (Compound 1)

To a 100 ml 3-necked round bottom flask (fitted with a glass stopper, reflux condenser, and a rubber septum) was added 25 ml of diethylamine (distilled over solid KOH). The solvent was degassed with a vigorous stream of argon gas for several minutes. To this solution was added 2.67 g (10.3 mmol) of 2-[[2-t-butyl-1-(2-tetrahydropyranoxy)]-4-phenyl]acetylene (Compound N) dissolved in 10 ml of diethylamine, 0.39 g (2.1 mmol) of cuprous iodide (ground to a powder), and 2.72 g (9.8 mmol) of ethyl 4-iodobenzoate (Compound A) dissolved in 5 ml of diethylamine. The resultant yellow solution was degassed for 10 minutes after which 1.67 g (2.4 mmol) of bis(triphenyl)phosphine palladium (II) chloride was added. The solution was cooled to 0° C., degassed for 5 minutes, and then stirred at 0° C. for 25 minutes. The reaction mixture was allowed to warm to room temperature and then stirred overnight. A salt formed against the walls of the flask. The reaction mixture was filtered through celite, washed with 500 ml of ethyl ether and the celite discarded. The filtrate was extracted with 200 ml of water and the layers were separated. The organic phase was washed with 3×200 ml-portions of water, washed once with 150 ml of brine solution, dried over K$_2$CO$_3$, filtered and concentrated in vacuo to yield a yellow foam. Purification by flash chromatography (silica, 5% ethyl acetate in hexane) followed by recrystallization from boiling methanol yielded the title compound as beige needles. PMR (CDCl$_3$): d 1.38 (3H, t, J=7.1 Hz), 1.43 (9H, s), 1.6–2.1 (6H, m), 3.6–3.7 (1H, m), 3.8–3.95 (1H, m), 4.38 (2H, q, J=7.1 Hz), 5.52 (1H, t, J=2.5 Hz), 7.16 (1H, d, J=8.5 Hz), 7.36 (1H, dd, J=8.5, 2.1 Hz), 7.48 (1H, d, J=2.1 Hz), 7.57 (2H, d, J=8.4 Hz), 8.01 (2H, d, J=8.4 Hz).

4-[2-[[2-t-Butyl-1-(2-tetrahydropyranoxy)]-4-phenyl]ethyn-1-yl]benzoic acid (Compound 2)

To a solution of 2.00 g (4.9 mmol) of ethyl 4-[2-[[2-t-butyl-1-(2-tetrahydropyranoxy)]-4-phenyl]ethyn-1-yl]benzoate (Compound 1) in 80 ml of tetrahydrofuran was added 19.7 ml (9.8 mmol) of a 0.5 M LiOH solution. The yellow, homogeneous solution was allowed to stir at room temperature for 19 hours. The reaction mixture was concentrated in vacuo, partitioned between 100 ml of water and 60 ml of hexane and the layers were separated. The aqueous phase was diluted with 200 ml of ethyl ether, cooled to 0° C. and acidified with 1 N sulfuric acid to an approximate pH of 4–5. The layers were separated and the aqueous layer was discarded. The organic phase was washed once with brine solution, dried over MgSO$_4$, filtered and concentrated in vacuo to yield a white solid. The solid was recrystallized from boiling acetonitrile to give the title compound as fine, white needles. PMR (CDCl$_3$): d 1.43 (9H, s), 1.6–2.1 (6H, m), 3.6–3.75 (1H, m), 3.8–3.95 (1H, m), 5.52 (1H, br s), 7.17 (1H, d, J=8.6 Hz), 7.37 (1H, dd, J=8.6, 2.0 Hz), 7.48 (1H, d, J=2.0 Hz), 7.60 (2H, d, J=8.6 Hz), 8.07 (2H, J=8.6 Hz).

Ethyl 6-[2-[[2-t-butyl-1-(2-tetrahydropyranoxy)]-5-phenyl]-ethyn-1-yl]nicotinoate (Compound 5)

Using the same procedure as for the preparation of ethyl 4-[2-[[2-t-butyl-1-(2-tetrahydropyranoxy)]-4-phenyl]-ethyn-1-yl]benzoate (Compound 1), but instead using 2.21 g (8.6 mmol) of 2-[[2-t-butyl-1-(2-tetrahydropyranoxy)]-5-phenyl]acetylene (Compound O), 0.45 g (2.4 mmol) of cuprous iodide (ground to a powder), 2.15 g (7.8 mmol) of ethyl 6-iodonicotinate (Compound C), 1.89 g (2.7 mmol) of bis(triphenyl)phosphine palladium (II) chloride and 45 ml of diethylamine stirred at room temperature overnight (27.5 hours) gave an orange foam. Purification by flash chromatography (pre-absorbed onto silica with chloroform, eluted with 10% ethyl acetate in hexane) followed by recrystallization from boiling methanol yielded the title compound as bright yellow, needles. PMR (CDCl$_3$): d 1.42 (3H, t, J=7 Hz), 1.42 (9H, s), 1.6–2.1 (6H, m), 3.65–3.8 (1H, m), 3.85–3.95 (1H, m), 4.43 (2H, q, J=7 Hz), 5.50 (1H, t, J=2.4 Hz), 7.21 (1H, dd, J=8.1, 1.7 Hz), 7.29 (1H, d, J=8.1 Hz), 7.44 (1H, d, J=1.7 Hz), 7.60 (1H, d, J=8.2 Hz), 8.29 (1H, dd, J=8.2, 2.2 Hz), 9.20 (1H, d, J=2.2 Hz).

Ethyl 4-[2-[[2-t-butyl-1-(2-tetrahydropyranoxy)]-5-phenyl]-ethyn-1-yl]benzoate (Compound 6)

Using the same procedure as for the preparation of ethyl 4-[2-[[2-t-butyl-1-(2-tetrahydropyranoxy)]-4-phenyl]-ethyn-1-yl]benzoate (Compound 1), but instead using 3.30 g (12.8 mmol) of 2-[[2-t-butyl-1-(2-tetrahydropyranoxy)]-5-phenyl]acetylene (Compound O), 0.44 g (2.3 mmol) of cuprous iodide (ground to a powder), 3.20 g (11.6 mmol) of ethyl 4-iodobenzoate (Compound A), 1.87 g (2.7 mmol) of bis(triphenyl)phosphine palladium (II) chloride and 50 ml of diethylamine gave, after aqueous work up, an orange foam. Purification by flash chromatography (preabsorbed onto silica with chloroform, eluted with 5% ethyl acetate in hexane) followed by recrystallization from boiling methanol yielded the title compound as light brown, clusters. PMR (CDCl$_3$): d 1.40 (3H, t, J=7.1 Hz), 1.42 (9H, s), 1.6–2.1 (6H, m), 3.6–3.75 (1H, m), 3.85–3.95 (1H, m), 4.38 (2H, q, J=7.1 Hz), 5.53 (1H, br s ), 7.11 (1H, dd, J=8.1, 2 Hz), 7.27 (1H, d, J=8.1 Hz), 7.36 (1H, d, J=2 Hz), 7.57 (2H, d, J=8.4 Hz), 8.01 (2H, d, J=8.4 Hz).

4-[2-[[2-t-Butyl-1-(2-tetrahydropyranoxy)]-5-phenyl]ethyn-1-yl]-1-benzoic acid (Compound 7)

Using the same procedure as for the preparation of 4-[2-[[2-t-butyl-1-(2-tetrahydropyranoxy)]-4-phenyl]ethyn-1-yl]benzoic acid (Compound 2), but instead using 2.01 g (5.1 mmol) of ethyl 4-[2-[[2-t-butyl-1-(2-tetrahydropyranoxy)]-5-phenyl]- ethyn-1-yl]benzoate (Compound 6), 10.5 ml (10.5 mmol) of 1.0 M LiOH solution and 44 ml of tetrahydrofuran (THF), the resulting solution was allowed to stir at room temperature for 48 hours. Thereafter it was refluxed overnight to give, after aqueous work up, a white solid. Purification by flash chromatography (silica, 10% ethyl acetate in hexane followed by 15% methanol in dichloromethane) yielded the title compound as an off-white solid. PMR (DMSO-d$_6$): d 1.39 (9H, s), 1.55–2.0 (6H, m), 3.6–3.8 (2H, m), 5.64 (1H, t,), 7.14 (1H, dd, J=8.0, 1.6 Hz), 7.26 (1H, d, J=1.6 Hz), 7.30 (1H, d, J=8.0 Hz), 7.62 (2H, d, J=8.3 Hz), 7.97 (2H, d, J=8.3 Hz).

6-[2-[[2-t-Butyl-1-(2-tetrahydropyranoxy)]-5-phenyl]ethyn-1-yl]nicotinic acid (Compound 8)

Using the same procedure as for the preparation of 4-[2-[[2-t-butyl-1-(2-tetrahydropyranoxy)]-4-phenyl]ethyn-1-yl]benzoic acid (Compound 2), but instead using 1.50 g (3.8 mmol) of ethyl 6-[2-[[2-t-butyl-1-(2-tetrahydropyranoxy)]-5-phenyl]ethyn-1-yl]nicotinoate (Compound 5), 8.0 ml (8.0 mmol) of a 1.0 M LiOH solution and 32 ml of tetrahydrofuran stirred at room temperature for 48 hours gave, after aqueous work up, a yellow solid. The solid was recrystallized from boiling acetonitrile to give the title compound as bright yellow crystals. PMR (DMSO-d$_6$): d 1.40 (9H, s), 1.55–2.0 (6H, m), 3.6–3.8 (2H, m), 5.65 (1H, br s), 7.21 (1H, dd, J=8, 1.7 Hz), 7.3–7.35 (2H, m), 7.77 (1H, d, J=8.2 Hz), 8.29 (1H, dd, J=8.2, 2.2 Hz), 9.06 (1H, d, J=2.2 Hz).

Ethyl (3-bromophenyl)acetate (Compound B$_1$)

100 g (463 mmol) of 3-bromophenylacetic acid was converted into the title compound (yellow oil) using 2 g of conc. H$_2$SO$_4$ and 500 ml of ethanol by refluxing the reaction for 16 hours. Thereafter, the reaction mixture was cooled to ambient temperature, stirred with solid K$_2$CO$_3$ for 30 minutes and then filtered. The filtrate was concentrated in vacuo, diluted with Et$_2$O, washed with 10% aqueous NaHCO$_3$ and brine, dried over MgSO$_4$ and concentrated in vacuo to give the title compound.

PMR (CDCl$_3$): δ 1.26 (3H, t, J=7.0 Hz), 3.56 (2H, s), 4.16 (2H, q, J=7.0 Hz), 7.16–7.26 (2H, m), 7.38–7.46 (2H, m).

Ethyl 4-(3-bromophenyl)butanoate (Compound D$_1$)

60 g (246 mmol) of ethyl(3-bromophenyl)acetate (Compound B$_1$) was converted into the title compound (oil) using 255 ml (255 mmol) of diisobutyl aluminum hydride (DIBAL-H, 1M in hexane), 85.8 g (250 mmol) of (carbethoxy methylene)triphenylphosphorane and 1.7 g of 10% Pd/C. The procedure was as follows: To a cold solution (−78° C.) of Compound B$_1$ in CH$_2$Cl$_2$ was added dropwise (over a span of 1 hour) the diisobutyl aluminum hydride (DIBAL-H, 1M solution in hexane). After the DIBAL-H addition was complete, the reaction was stirred at −78 ° C. for an additional hour. The reaction was quenched by the dropwise addition of methanol, followed by water and 10% HCl. The mixture was then warmed to 0° C., stirred for 10 minutes and then washed with water, 10% aqueous NaHCO$_3$ and brine. The organic phase was dried over MgSO$_4$ and the solvent distilled off at ambient temperature to give crude (3-bromophenyl)acetaldehyde. To a cold solution (0° C.) of this crude aldehyde in CH$_2$Cl$_2$ was added a solution of the (carbethoxy methylene)triphenylphosphorane reagent in CH$_2$Cl$_2$. The mixture was stirred for 16 hours, concentrated in vacuo and purified by flash chromatography (silica, 10% EtOAc-hexane) to give ethyl 4-(3-bromophenyl)but-2-enoate as a mixture of E:Z isomers. This isomeric mixture was dissolved in EtOAc and hydrogenated over 10% Pd/C for 6 hours. The catalyst was filtered off and the filtrate concentrated in vacuo to give the title compound as a white solid.

PMR (CDCl$_3$): δ 1.26 (3H, t, J=7.1 Hz), 1.89–2.00 (2H, m), 2.31 (2H, t, J=7.5 Hz), 2.63 (2H, t, J=7.2 Hz), 4.15 (2H, q, J=7.1 Hz), 7.10–7.35 (4H, m).

5-(3-bromophenyl)-2-methylpentan-2-ol (Compound E$_1$)

To a cold solution (0° C.) of 17 g (63 mmol) of ethyl 4-(3-bromophenyl)butanoate (Compound D$_1$) in 40 ml of THF was added 63 ml (189 mmol) of methylmagnesium bromide (3.0M solution in THF). The reaction was stirred at 0° C. for 2 hours, quenched by the slow addition of ice cold water (30 ml) followed by 10% HCl (30 ml) and then extracted with Et$_2$O (4×60 ml). The combined organic layer was washed with 10% aqueuos NaHCO$_3$ (10 ml), water (10 ml) and brine (10 ml), dried over MgSO$_4$ and concentrated in vacuo. Purification by kugelrohr distillation gave the title compound as a colorless oil.

PMR (CDCl$_3$): δ 1.20 (6H, s), 1.43–1.55 (2H, m), 1.62–1.78 (2H, m), 2.60 (2H, t, J=6.0 Hz), 7.10–7.41 (4H, m).

6-Bromo-1,2,3,4-tetrahydro-1,1-dimethylnaphthalene (Compound $F_1$)

15.0 g (58.3 mmol) of 5-(3-bromophenyl)-2-methylpentan-2-ol (Compound $E_1$) was cooled to 0° C. and then 2.8 ml of conc. $H_2SO_4$ was added. The mixture was stirred for 2.5 hours, diluted with water (20 ml) and extracted with $Et_2O$ (3×40 ml). The combined organic layers were washed with water, sat. aqueous $NaHCO_3$ and brine, dried over $MgSO_4$ and concentrated in vacuo. Purification by kugelrohr distillation gave the title compound as a colorless oil.

PMR ($CDCl_3$): δ 1.25 (6H, s), 1.61–1.66 (2H, m), 1.74–1.82 (2H, m), 2.73 (2H, t, J=6.0 Hz), 7.16–7.26 (3H, m).

7-Bromo-3,4-dihydro-4,4-dimethyl-naphthalen-1(2H)-one (Compound $G_1$)

To a cold mixture (0° C.) of 209 g (200 mmol) of chromium trioxide, 100 ml (1.06 mol) of acetic anhydride and 200 ml (3.5 mol) of acetic acid was added a solution of 10 g (41.8 mmol) of 6-bromo-1,2,3,4-tetrahydro-1,1-dimethylnaphthalene (Compound $F_1$) in 125 ml of benzene. The reaction mixture was stirred for 1 hour, quenched with ice cold water and extracted with $Et_2O$ (3×100 ml). The organic layer was dried over $MgSO_4$, concentrated in vacuo, and purified by column chromatography (silica, 10% EtOAc-hexane) to give the title compound as a white solid.

PMR ($CDCl_3$): δ 1.28 (6H, s), 2.01 (2H, t, J=6.0 Hz), 2.72 (2H, t, J=6.0 Hz), 7.31 (1H, d, J=9.0 Hz), 7.61 (1H, dd, J=3.0, 9.0 Hz), 8.11 (1H, d, J=3.0 Hz).

7-Ethynyl-3,4-dihydro-4,4-dimethyl-naphthalen-1(2H)-one (Compound $L_1$)

7 g (27.6 mmol) of 7-bromo-3,4-dihydro-4,4-dimethyl-naphthalen-1(2H)-one (Compound $G_1$) was converted into the title compound using 39 ml (36.6 mmol) of trimethylsilyl acetylene, 0.97 g (1.3 mmol) of bis(triphenylphosphine) palladium(II) chloride, 0.26 g (1.3 mmol) of cuprous iodide and 0.6 g (4.3 mmol) of $K_2CO_3$. The procedure was as follows: To a solution, flushed for 15 minutes with a stream of argon, of Compound $G_1$ in triethylamine was added the bis(triphenylphosphine)palladium(II) chloride and cuprous iodide. The solution mixture was flushed with argon for 5 minutes and then the trimethylsilyl acetylene was added. The reaction mixture was sealed in a pressure tube and placed in a preheated oil bath (100° C.) for 24 hours. The reaction mixture was then filtered through celite, washed with $Et_2O$ and the filtrate concentrated in vacuo to give crude 7-(2-trimethylsilyl)ethynyl-3,4-dihydro- 4,4-dimethyl-naphthalen-1(2H)-one. To a solution of this crude TMS-acetylenic compound in methanol was added $K_2CO_3$. The mixture was stirred for 8 hours at ambient temperature and then filtered. The filtrate was concentrated in vacuo, diluted with $Et_2O$, washed with water, 10% HCl and brine, dried over $MgSO_4$ and concentrated in vacuo. Purification by column chromatography (silica, 10% EtOAc-hexane) yielded the title compound as a white solid.

PMR ($CDCl_3$): δ 1.39 (6H, s), 2.02 (2H, t, J=7.0 Hz), 2.73 (2H, t, J=7.0 Hz), 3.08 (1H, s), 7.39 (1H, d, J=8.2 Hz), 7.61 (1H, dd, J=1.8 , 8.2 Hz), 8.14 (1H, d, J=9 1.8 Hz).

Ethyl 4-[(5,6,7,8-tetrahydro-8,8-dimethyl-5-oxonaphth-3-yl)ethynyl]benzoate (Compound 9)

4 g (21.7 mmol) of 7-ethynyl-3,4-dihydro-4,4-dimethyl-naphthalen-1(2H)-one (Compound $L_1$) was converted into the title compound using 6 g (21.7 mmol) of ethyl 4-iodobenzoate, 5 g (7.2 mmol) of bis(triphenylphosphine) palladium(II) chloride and 1.4 g (7.2 mmol) of cuprous iodide. The procedure was as follows: To a solution of Compound $L_1$, flushed for 15 minutes with a stream of argon, and ethyl 4-iodobenzoate in triethylamine was added the bis(triphenylphosphine)palladium(II) chloride catalyst and the cuprous iodide. The solution mixture was flushed with argon for 5 minutes and then stirred at ambient temperature for 18 hours. The reaction mixture was filtered through celite and the filtrate concentrated in vacuo. Purification by flash chromatography (silica, 10% EtOAc-hexane) yielded the title compound as a white solid.

PMR ($CDCl_3$): δ 1.41 (3H, t, J=7.2 Hz), 1.41 (6H, s), 2.04 (2H, t, J=6.5 Hz), 2.76 (2H, t, J=6.5 Hz), 4.40 (2H, q, J=7.2 Hz), 7.44 (1H, d, J=8.2 Hz), 7.59 (2H, d, J=8.4 Hz), 7.68 (1H, dd, J=1.8, 8.2 Hz), 8.04 (2H, d, J=8.4 Hz), 8.15 (1H, d, J=1.8 Hz).

Ethyl 4-[(5,6,7,8-tetrahydro-5-hydroxy-8,8-dimethylnaphth-3-yl)ethynyl]benzoate (Compound 10)

1 g (2.88 mmol) of ethyl 4-[(5,6,7,8-tetrahydro-8,8-dimethyl-5-oxonaphth-3-yl)ethynyl]benzoate (Compound 9) was converted into the title compound using 60 mg (1.6 mmol) of sodium borohydride. The procedure was as follows: To a cold solution (0° C.) of Compound 9 in 5 ml of THF and 10 ml of ethanol was added sodium borohydride. The mixture was stirred for 6 hours, diluted with water (10 ml) and extracted with $Et_2O$ (4×40 ml). The combined organic layers were washed with 10% HCl (5 ml), 10% aqueous $NaHCO_3$ (10 ml) and brine (10 ml), dried over $MgSo_4$ and concentrated in vacuo to give the title compound as a white solid.

PMR ($CDCl_3$): δ 1.26 (3H, s), 1.33 (3H, s), 1.40 (3H, t, J=7.1 Hz), 1.58–1.70 (1H, m), 1.80–1.95 (2H, m), 2.04–2.14 (1H, m), 4.38 (2H, q, J=7.1 Hz), 4.72 (1H, q, J=5.1 Hz), 7.32 (1H, d, J=8.2 Hz), 7.41 (1H, dd, J=1.8, 8.2 Hz), 7.56 (2H, d, J=8.5 Hz), 7.65 (1H, d, J=1.8 Hz), 8.01 (2H, d, J=8.5 Hz).

Ethyl 4-[[5,6,7,8-tetrahydro-5(RS)-(2'(RS)-tetrahydropyranyloxy)-8,8-dimethylnaphth-3-yl]ethynyl]benzoate (Compound 11) and Ethyl 4-[[5,6,7,8-tetrahydro-5(RS)-(2'(SR)-tetrahydropyranyloxy)-8,8-dimethylnaphth-3-yl]ethynyl]benzoate (Compound 12)

500 mg (1.44 mmol) of ethyl 4-[(5,6,7,8-tetrahydro-5-hydroxy-8,8-dimethylnaphth-3-yl)ethynyl]benzoate (Compound 10) was converted to a mixture of diastereomers using 400 mg (4.8 mmol) of 3,4-dihydro-2H-pyran and 50 mg (0.2 mmol) of pyridinium p-toluenesulfonate. The procedure was as follows: To a cold solution (0° C.) of Compound 10 in $CH_2Cl_2$ was added 3,4-dihydro-2H-pyran (DHP) followed by the pyridinium p-toluenesulfonate (PPTS) catalyst. The reaction mixture was stirred at ambient temperature for 16 hours and then 1 g of $K_2CO_3$ was added. The mixture was stirred for 5 minutes, washed with water and brine, dried over $MgSO_4$ and concentrated in vacuo to a gummy mixture of two diastereomers. HPLC separation (Partisil 10, 10% EtOAc-hexane) of the diastereomers gave the title compounds (RT=65 and 70 minutes), respectively.

Ethyl 4-[[5,6,7,8-tetrahydro-5(RS)-(2'(RS)-tetrahydropyranyloxy)-8,8-dimethylnaphth-3-yl]ethynyl]benzoate (Compound 11)

PMR ($CDCl_3$): (RT=65 minutes) δ 1.26 (3H,s), 1.32 (3H,s), 1.43 (3H, t, J=7.1 Hz), 1.51–2.20 (10H, m), 3.55–3.62 (1H, m), 3.95–4.05 (1H, m), 4.39 (2H, q, J=7.1 Hz), 4.64 (1H, t, J=5.9 Hz), 4.89 (1H, t, J=2.9 Hz), 7.33 (1H, d, J=8.2 Hz), 7.41 (1H, dd, J=1.8, 8.2 Hz), 7.46 (1H, d, J=1.8 Hz), 7.57 (2H, d, J=8.2 Hz), 8.01 (2H, d, J=8.2 Hz).

Ethyl 4-[[5,6,7,8-tetrahydro-5(RS)-(2'(SR)-tetrahydropyranyloxy)-8,8-dimethylnaphth-3-yl]ethynyl]benzoate (Compound 12)

PMR ($CDCl_3$): (RT=70 minutes) δ 1.26 (3H,s), 1.32 (3H,s), 1.40 (3H, t, J=7.1 Hz), 1.52–1.68 (5H, m), 1.72–1.95 (4H, m), 1.96–2.10 (1H, m), 3.55–3.65 (1H, m), 4.00–4.10

(1H, m), 4.38 (2H, q, J=7.1 Hz), 4.77 (1H, t, J=6.1 Hz), 4.89 (1H, t, J=2.5 Hz), 7.30 (1H, d, J=8.2 Hz), 7.40 (1H, dd, J=1.8, 8.2 Hz), 7.57 (2H, d, J=8.5 Hz), 7.68 (1H, d, J=1.8 Hz),8.01 (2H, d, J=8.5 Hz).

4-[[5,6,7,8-tetrahydro-5(RS)-(2'(RS)-tetrahydropyranyloxy)-8,8-dimethylnaphth-3-yl]ethynyl] benzoic acid (Compound 13)

80 mg (0.19 mmol) of ethyl 4-[[5,6,7,8-tetrahydro-5(RS)-(2'(RS)-tetrahydropyranoxy)-8,8-dimethylnaphth-3-yl] ethynyl]benzoate (Compound 11) was converted into the title compound using 1 ml (1 mmol) of LiOH (1M aqueous solution). The procedure was as follows: To a solution of Compound 11 in 3 ml of THF and 1 ml of methanol was added LiOH (1M aqueous solution). The mixture was refluxed for 2 hours, cooled to ambient temperature, diluted with 100 ml of Et$_2$O:EtOAc (1:1, v/v) and acidified to pH 5 with ice-cold 10% HCl. The organic phase was washed with water (10 ml) and brine (10 ml), dried with MgSO$_4$ and concentrated in vacuo to yield the title compound as a white solid.

PMR (CDCl$_3$): δ 1.26 (3H, s), 1.33 (3H, s), 1.60–2.10 (10H, m), 3.55–3.65 (1H, m), 3.95–4.05 (1H, m), 4.65 (1H, t, J=5.5 Hz), 4.90 (1H, t, J=2.9 Hz), 7.34 (1H, d, J=8.2 Hz), 7.42 (1H, dd, J=1.8, 8.2 Hz), 7.46 (1H, d, J=1.8 Hz), 7.61 (2H, d, J=8.2 Hz), 8.07 (2H, d, J=8.2 Hz).

4-[[5,6,7,8-tetrahydro-5(RS)-(2'(SR)-tetrahydropyranyloxy)-8,8-dimethylnaphth-3-yl]ethynyl] benzoic acid (Compound 14)

Employing the same general procedure as for the preparation of 4-[[5,6,7,8-tetrahydro-5(RS)-(2'(RS)-tetrahydropyranyloxy)-8,8-dimethylnaphth-3-yl]ethynyl] benzoic acid (Compound 13), 100 mg (0.23 mmol) of ethyl 4-[[5,6,7,8-tetrahydro-5(RS)-(2'(SR)-tetrahydropyranoxy)-8,8-dimethylnaphth-3-yl]ethynyl]benzoate (Compound 12) was converted into the title compound using 0.6 ml (0.6 mmol) of LiOH (1M aqueous solution).

PMR (DMSO-d$_6$): δ 1.22 (3H, s), 1.27 (3H, s), 1.40–1.60 (5H, m), 1.62–1.86 (4H, m), 1.90–2.05 (1H, m), 3.50–3.60 (1H, m), 3.87–4.00 (1H, m), 4.68 (1H, t, J=5.5 Hz), 4.80–4.85 (1H, m), 7.45 (2H, s), 7.54 (1H, s), 7.67 (2H, d, J=8.4 Hz), 7.97 (2H, d, J=8.4 Hz).

What is claimed is:

1. A method for treating a mammal, in need of such treatment, with a pharmaceutical composition containing as its active ingredient an effective amount of a compound capable of binding AP1 protein in a complex with said compound and with a retinoid receptor thereby inhibiting gene expression promoted by AP1 protein, said compound substantially unable to activate gene expression induced through binding of said compound to RARα and RARΓ retinoid receptors.

2. A method in accordance with claim 1 wherein in a transactivation assay utilized for measuring the ability of said compound to transactivate gene expression through RARα, RARβ and RARΓ receptors, the compound is at least 20 times less active through RARα and through RARΓ receptors than through RARβ receptors.

3. A method for treating a mammal, in need of such treatment, with a pharmaceutical composition containing as its active ingredient an effective amount of a compound capable of binding AP1 protein in a complex with said compound and with a retinoid receptor thereby inhibiting gene expression promoted by AP1 protein, said compound substantially unable to activate gene expression induced through binding of said compound to RARα and RARγ retinoid receptors where the active ingredient comprises a compound selected from formula 1 and formula 2

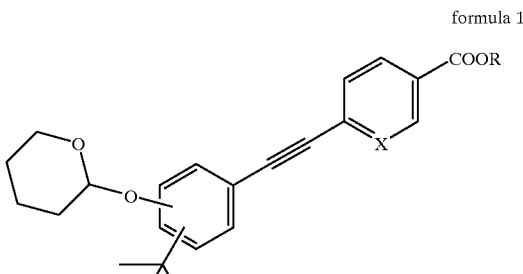

formula 1

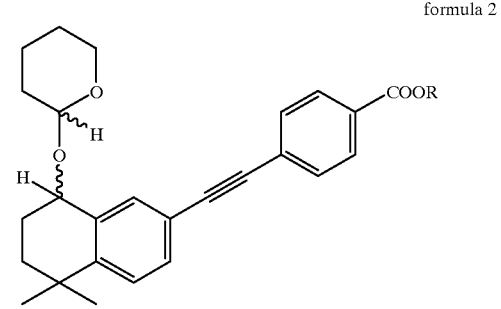

formula 2 where X is N or CH, and R is H, or lower alkyl, or a pharmaceutically acceptable salt of said compound.

4. A method in accordance with claim 3 where R is H or a pharmaceutically acceptable salt thereof.

5. A method in accordance with claim 3 where R is $C_1$–$C_3$ alkyl.

6. A method in accordance with claim 3 wherein the compound is in accordance with formula 1.

7. A method in accordance with claim 6 wherein the compound is selected from the group consisting of:

(1) 4-[2-[[2-t-butyl-1-(2-tetrahydropyranoxy)]-4-phenyl] ethyn-1-yl]benzoic acid;

(2) 4-[2-[[2-t-butyl-1-(2-tetrahydropyranoxy)]-5-phenyl]-ethyn-1-yl]-1-benzoic acid, and (3) 6-[2-[[2-t-butyl-1-(2-tetrahydropyranoxy)]-5-phenyl] ethyn-1-yl]nicotinic acid.

8. A method in accordance with claim 3 wherein the compound is in accordance with formula 2.

9. A method in accordance with claim 7 wherein the compound is selected from the group consisting of:

(1) 4-[[5,6,7,8-tetrahydro-5(RS)-(2'(RS)-tetrahydropyranyloxy)-8,8-dimethylnaphth-3-yl]ethynyl]benzoic acid, and (2) 4-[[5,6,7,8-tetrahydro-5(RS)-(2'(SR)-tetrahydropyranyloxy)-8,8-dimethylnaphth-3-yl]ethynyl]benzoic acid.

10. A method for repressing expression of AP1 protein responsive gene in a mammal in need of such repression for a therapeutic purpose, without significantly activating expression of genes which are activated through RARα and RARΓ retinoid receptors, said method comprising administering to said mammal a retinoid compound capable of binding AP1 protein in a complex with said compound and with a retinoid receptor thereby inhibiting gene expression promoted by AP1 protein, said compound substantially unable to activate gene expression promoted by RARα and RARΓ retinoid receptors.

11. A method in accordance with claim 10 wherein in a transactivation assay utilized for measuring the ability of said compound to transactivate gene expression through RARα, RARβ and RARΓ receptors, the compound is at least 20 times less active through RARα and through RARΓ receptors than through RARβ receptors.

12. A method for repressing expression of AP1 protein responsive gene in a mammal in need of such repression for a therapeutic purpose, without significantly activating expression of genes which are activated through RARα and RARγ retinoid receptors, said method comprising administering to said mammal a retinoid compound capable of binding AP1 protein in a complex with said compound and with a retinoid receptor thereby inhibiting gene expression promoted by AP1 protein, said compound substantially unable to activate gene expression promoted by RARα and RARγ retinoid receptors where the active ingredient comprises a compound selected from formula 1 and formula 2

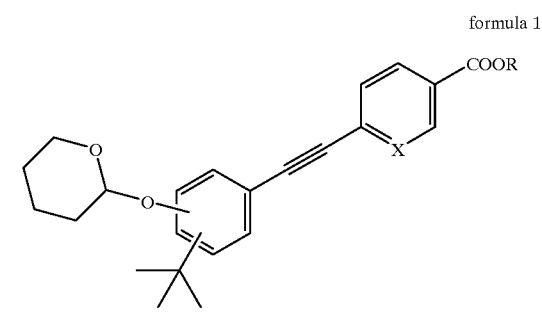

formula 1

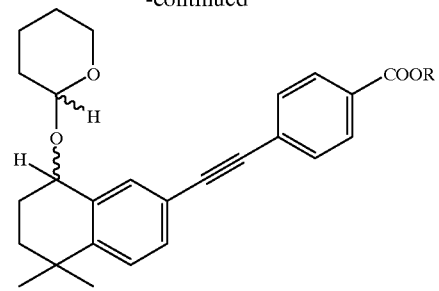

-continued formula 2 where X is N or CH, and R is H, or lower alkyl, or a pharmaceutically acceptable salt of said compound.

13. A method in accordance with claim 12 where R is H or a pharmaceutically acceptable salt thereof.

14. A method in accordance with claim 12 where R is $C_1$–$C_3$ alkyl.

15. A method in accordance with claim 12 wherein the compound is in accordance with formula 1.

16. A method in accordance with claim 15 wherein the compound is selected from the group consisting of:
(1) 4-[2-[[2-t-butyl-1-(2-tetrahydropyranoxy)]-4-phenyl]ethyn-1-yl]benzoic acid;
(2) 4-[2-[[2-t-butyl-1-(2-tetrahydropyranoxy)]-5-phenyl]-ethyn-1-yl]-1-benzoic acid, and
(3) 6-[2-[[2-t-butyl-1-(2-tetrahydropyranoxy)]-5-phenyl]ethyn-1-yl]nicotinic acid.

17. A method in accordance with claim 12 wherein the compound is in accordance with formula 2.

18. A method in accordance with claim 17 wherein the compound is selected from the group consisting of:
(1) 4-[[5,6,7,8-tetrahydro-5(RS)-(2'(RS)-tetrahydropyranyloxy)-8,8-dimethylnaphth-3-yl]ethynyl]benzoic acid, and
(2) 4-[[5,6,7,8-tetrahydro-5(RS)-(2'(SR)-tetrahydropyranyloxy)-8,8-dimethylnaphth-3-yl]ethynyl]benzoic acid.

* * * * *

UNITED STATES PATENT AND TRADEMARK OFFICE
CERTIFICATE OF CORRECTION

PATENT NO. : 6,025,388
DATED : February 15, 2000
INVENTOR(S) : Nagpal et al.

Page 1 of 2

It is certified that error appears in the above-identified patent and that said Letters Patent is hereby corrected as shown below:

Column 1, line 39, "Darier's" should be --Darrier's--.

Column 3, line 50, "Darier's" should be --Darrier's--.

Column 10, line 17, "ul" should be --μL--.

Column 10, line 18, "ul" should be --μL--.

Column 13, line 6, "examplary" should be --exemplary--.

Column 14, line 40, "it" shuldbe --its--.

Column 18, line 11, "dichlomethane" should be --dichloromethane--.

Column 21, line 30, "d" should be --δ--.

Column 21, line 46, "d 7.90" should be --δ 7.90--.

Column 21, line 65, "d" should be --δ--.

Column 22, line 19, "d 1.37" should be --δ 1.37--.

Column 22, line 35, "d" should be --δ--.

Column 22, line 53, "d" should be --δ--.

Column 23, line 5, "d" should be --δ--.

Column 23, line 49, "d" should be --δ--.

Column 24, line 12, "d" should be --δ--.

UNITED STATES PATENT AND TRADEMARK OFFICE
CERTIFICATE OF CORRECTION

PATENT NO. : 6,025,388
DATED : February 15, 2000
INVENTOR(S) : Nagpal et al.

It is certified that error appears in the above-identified patent and that said Letters Patent is hereby corrected as shown below:

Column 24, line 44, "d" should be --$\delta$--.

Column 24, line 67, "d" should be --$\delta$--.

Column 25, line 19, "d" should be --$\delta$--.

Column 25, line 40, "d" should be --$\delta$--.

Column 25, line 59, "d" should be --$\delta$--.

Column 26, line 8, "d" should be --$\delta$--.

Signed and Sealed this

Eighth Day of May, 2001

Attest:

NICHOLAS P. GODICI

Attesting Officer   Acting Director of the United States Patent and Trademark Office